United States Patent [19]
Curtiss, III et al.

[11] Patent Number: 5,855,880
[45] Date of Patent: Jan. 5, 1999

[54] AVIRULENT MICROBES AND USES THEREFOR

[75] Inventors: Roy Curtiss, III; Sandra M. Kelly, both of St. Louis, Mo.

[73] Assignee: Washington University, St. Louis, Mo.

[21] Appl. No.: 596,732

[22] Filed: Feb. 5, 1996

Related U.S. Application Data

[60] Division of Ser. No. 209,542, Mar. 10, 1994, which is a continuation-in-part of Ser. No. 612,001, Nov. 9, 1990, abandoned, which is a continuation-in-part of Ser. No. 200,934, Jun. 1, 1988, abandoned, which is a continuation-in-part of Ser. No. 58,360, Jun. 4, 1987, abandoned, said Ser. No. 200,934, is a continuation-in-part of Ser. No. 251,304, Oct. 3, 1988, abandoned, which is a continuation-in-part of Ser. No. 106,072, Oct. 7, 1987, abandoned.

[51] Int. Cl.$^6$ .................. A61K 39/02; A61K 39/112; C12N 1/21
[52] U.S. Cl. .................. 424/93.2; 424/93.48; 424/184.1; 424/200.1; 424/235.1; 424/257.1; 424/258.1; 435/172.3; 435/252.3; 435/252.33; 435/320.1; 435/879
[58] Field of Search .................. 435/172.3, 320.1, 435/252.3, 252.33, 879; 424/93.2, 93.48, 184.1, 200.1, 235.1, 258.1, 257.1

[56] References Cited

U.S. PATENT DOCUMENTS 4,190,495  2/1980  Curtis .................. 435/172.3
4,837,151  6/1989  Stocker .................. 435/172.3

OTHER PUBLICATIONS

Komeda et al., Molec. Gen. Genet. vol. 142, 289–298 (1975).
Ferrari et al., Biotechnology, vol. 3, Nov. 1985, pp. 1003–1007.
Jagusztyn–Krynicka et al., Journal of General Microbiology (1982) pp.1135–1145.

*Primary Examiner*—Laurie Scheiner
*Attorney, Agent, or Firm*—Howell & Haferkamp, L.C.

[57] ABSTRACT

This invention provides immunogenic compositions for the immunization of a vertebrate or invertebrate comprising an avirulent derivative of *S. typhi*. The derivatives having a mutation of the cya and/or crp and/or cdt genes. The invention also provides immunogenic compositions for the immunization of a vertebrate and invertebrate comprising an avirulent derivative of the above type which is capable of expressing a recombinant gene derived from a pathogen of said vertebrate or invertebrate individual to produce an antigen capable of inducing an immune response against said pathogen. Other embodiments of the invention include methods of preparing immunogenic compositions from these strains, and strains useful in the preparation of the immunogenic compositions, as well as methods of stimulating the immune system to respond to an immunogenic antigen of *S. typhi* by administration of the immunogenic composition.

9 Claims, 6 Drawing Sheets

AVIRULENT MICROBES AND USES THEREFOR

CROSS-REFERENCE TO RELATED APPLICATIONS

This application is a divisional of U.S. application Ser. No. 08/209,542, filed Mar. 10, 1994; abandoned which is a continuation-in-part of U.S. application Ser. No. 07/612, 001, filed Nov. 9, 1990, now abandoned; which is a continuation in part of U.S. application Ser. No. 07/200,934, filed Jun. 1, 1988, now abandoned, which is a continuation-in-part of U.S. application Ser. No. 07/058,360, filed Jun. 4, 1987, now abandoned; U.S. application Ser. No. 07/200,934 is also a continuation-in-part of U.S. application Ser. No. 07/251,304, filed Oct. 3, 1988, now abandoned, which is a continuation-in-part of U.S. application Ser. No. 07/106, 072, filed Oct. 7, 1987, now abandoned. These applications are hereby incorporated herein by reference.

FIELD OF THE INVENTION

This invention relates to avirulent microbes, their method of preparation, and their use in vaccines. More specifically, it relates to avirulent *S. tydhi*.

BACKGROUND OF THE INVENTION

Typhoid fever, which is caused by *Salmonella typhi*, remains an important public health problem for residents in the less developed world, for travelers from industrialized countries who visit endemic areas, and for clinical microbiologists in laboratories which conduct proficiency tests. The currently licensed parenteral killed whole cell typhoid vaccines are protective but cause marked systemic and local adverse reactions at an unacceptably high frequency (Levine, Typhoid fever vaccines, in Plotkin S A, Mortimer E A Jr. (eds): VACCINES. Philadelphia, W B Saunders, 1988, pp. 333–361). Alternative vaccines include the recently licensed live oral vaccine strain Ty21a and the experimental parenteral Vi polysaccharide vaccine.

The advantage of an oral vaccine is the delivery of replicating organisms to the mucosal immune system where local responses are maximally stimulated. In addition, attenuated *Salmonella typhi* are attractive candidates to serve as carrier vaccines to express foreign antigens and deliver them to the human immune system. However, a critical prerequisite for successfully using this approach in immunizing humans is that there must exist highly immunogenic yet safe attenuated strains of *S. typhi* to deliver the foreign protein and polysaccharide antigens to the immune system.

The current oral vaccine based upon Ty21a has several disadvantages. Ty21a is of relatively low immunogenicity and requires multiple oral doses to immunize. The yield of viable organisms is low when it is fermented and lyophilized in large-scale. In addition, Ty21a has multiple mutations in addition to galE and via, which remain undefined. (Hone et al. (1987), J. Infect. Dis. 156:167–174; Hone et al. (1988), J. Infect. Immun. 56:1326–1333).

Constructs of Ty21a expressing the O antigen of *Shigella sonnei* (Formal et al. (1981), Infect. Immun. 34:746–750) or the O antigen of *Vibrio cholerae* 01 serotype Inaba (Forrest et al. (1989), J. Infect. Dis. 159:145–146) have undergone clinical testing in humans. Although two lots of the Ty21a/*S. sonnei* construct tested in North American volunteers provided significant protection against experimental challenge with pathogenic *S. sonnei*, there was lot-to-lot variation and other lots were not protective (Black et al. J. Infect. Dis. (1987), 155:1260–1267; Herrington et al. (1990), Vaccine 8:353–357). The Ty21a/Inaba construct elicited serum Inaba vibriocidal antibodies and intestinal SIgA anti-Inaba O antibodies in only a minority of vaccines and at low titer (Tacket et al. (1990), Infect. Immun. 1620–1627). In experimental challenge studies with pathogenic *V. cholerae* 01, recipients of the construct were not significantly protected overall against diarrhea, but did have milder diarrhea and shed fewer wild-type *V. cholerae* cells (Tacket et al., Id.).

The main drawbacks to the use of Ty21a as a candidate carrier strain include its limited immunogenicity, a lack of precise information on the molecular basis of its attenuation and practical difficulties in bacterial genetic manipulation of the strain (e.g., in transformation, electroporation, and recombination frequency). It also exhibits very poor viability after reconstitution of lyophilized cultures.

Applicant has discovered new methods of protecting against virulent infections with vaccines employing transposon-induced avirulent mutants of virulent agents in which the impairment leading to avirulence cannot be repaired by diet or by anything supplied by an animal host. Some of Applicant's initial work, including a method for creating an avirulent microbe by the introduction of deletion mutations in the adenylate cyclase gene (cya) and the cyclic AMP receptor protein gene (crp) of *Salmonella typhimurium* is described in EPO Pub. No. 315,682 (published 17 May, 1989), and PCT Pub. No. WO 88/09669 (published 15 Dec., 1988). Applicant has also provided methods for producing other types of avirulent mutant cells which are desirable as carrier cells for the expression of recombinant antigens. These cells are characterized by a lack of a functioning native gene encoding an enzyme which is essential for cell survival, wherein the enzyme catalyses a step in the biosynthesis of an essential cell wall structural component and the presence of a first recombinant gene encoding an enzyme which is a functional replacement for the native enzyme, wherein the first recombinant gene cannot replace the defective chromosomal gene. In these cells, the first recombinant gene is structurally linked to a second recombinant gene encoding a desired product. Loss of the first recombinant gene causes the cells to lyse. These methods are described in WO 89/03427 (published 20 Apr., 1989). The disclosures of the above-described patent applications, as well as any corresponding national patent applications, are incorporated herein by reference.

BRIEF DESCRIPTION OF THE INVENTION

The present invention is based, in part, on new avirulent *S. typhi* derivatives that are not disclosed in EPO Pub. No. 315,682. Included within the invention is the application of these new *S. typhi* derivatives in, inter alia, commercial vaccines, methods of stimulating the immune system to respond to an immunogenic antigen of *S. typhi*, and methods of stimulating the immune system to respond to an immunogenic antigen of a pathogen. The strains provided herein are directly and indirectly suitable for the production of commercial vaccines to prevent diseases caused by *S. typhi*, and other enteric bacteria with which antibodies to *S. typhi* cross react. These strains are also useful as carrier microorganisms for the production of expression products encoded on recombinant genes in the bacterial cells.

Accordingly, one embodiment of the invention is an immunogenic composition for the immunization of an individual comprising an avirulent derivative of *Salmonella typhi* (*S. typhi*) with a mutation in a cya gene, in a physiologically acceptable excipient.

Another embodiment of the invention is an isolated avirulent strain of S. typhi with a mutation in a cya gene.

Yet another embodiment of the invention is an immunogenic composition for the immunization of an individual comprising an avirulent derivative of S. typhi with a mutation in a crp gene.

Still another embodiment of the invention is an isolated avirulent strain of S. typhi with a mutation in a crp gene.

Another embodiment of the invention is an immunogenic composition for the immunization of an individual comprising an avirulent derivative of S. typhi, said derivative with a mutation in a cya gene and a mutation in a crp gene.

Yet another embodiment of the invention is an isolated avirulent strain of S. typhi with a mutation in a cya gene and a crp gene.

Still another embodiment of the invention is an immunogenic composition for the immunization of an individual comprising an avirulent derivative of Salmonella with a mutation in a cdt gene.

Another embodiment of the invention is an isolated avirulent strain of Salmonella which contains a mutation in a cdt gene.

Still another embodiment of the invention is an isolated strain selected from the group of strains $\chi3958$, $\chi4323$, $\chi3926$, $\chi3927$, $\chi4297$, $\chi4346$, $\chi3940$, $\chi4073$, and derivatives thereof.

Another embodiment of the invention is a method of utilizing a strain of avirulent S. typhi which is comprised of a mutation in a cya gene, the method comprising preparing an immunogenic composition by suspending the strain in a physiologically acceptable excipient.

Yet another embodiment of the invention is a method of utilizing a strain of avirulent S. typhi which is comprised of a mutation in a crp gene, the method comprising preparing an immunogenic composition by suspending the strain in a physiologically acceptable excipient.

Still another embodiment of the invention is a method of utilizing a strain of avirulent Salmonella which is comprised of a mutation in a cdt gene, the method comprising preparing an immunogenic composition by suspending the strain in a physiologically acceptable excipient.

Another embodiment of the invention is an isolated strain of S. typhi which is a cdt mutant.

BRIEF DESCRIPTION OF THE DRAWINGS

FIG. 1.B. is a graph which shows the recovery of CFU from the spleens of 8-week-old BALB/c female mice at specified times after peroral inoculation with $9 \times 10^8$ CFU of $\chi3622$ ($\Delta$[crp-cysG]-10), $1 \times 10^9$ CFU of $\chi3737$ (pSD110$^+$/ $\Delta$[crp-cysG]-10) and $1 \times 10^9$ CFU of $\chi3339$ (wild type). Three mice were sacrificed for each time point. The results are given as geometric means±standard deviations.

MODES FOR CARRYING OUT THE INVENTION

Figure 1A:
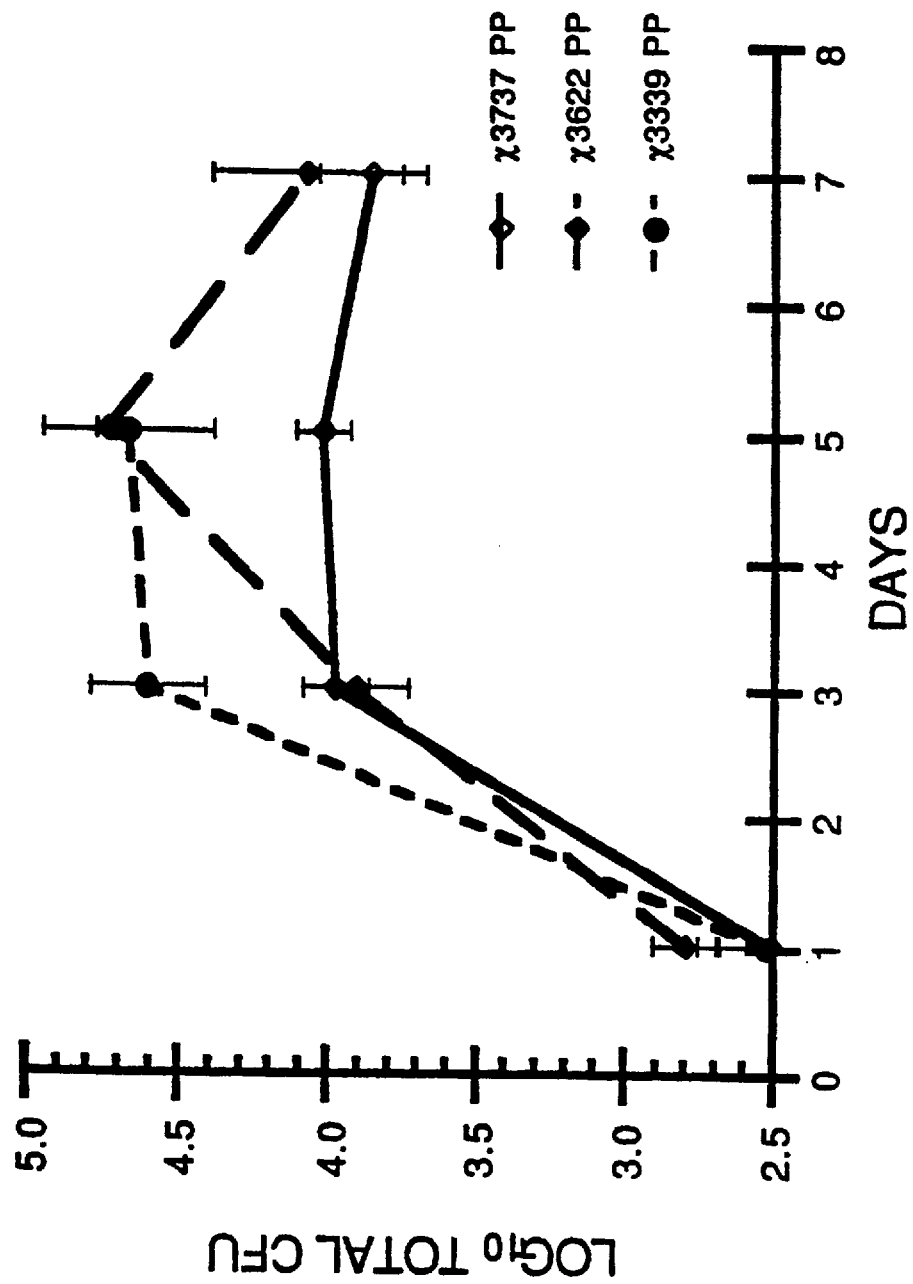
FIG. 1.A. is a graph which shows the recovery of CFU from the Peyer's patches of 8 week old BALB/c mice at specified times after peroral inoculation with $9 \times 10^8$ CFU of $\chi3622$ ($\Delta$[crp-cysG]-10), $1 \times 10^9$ CFU of $\chi3737$ (pSD110$^+$/ $\Delta$[crp-cysG]-10) and $1 \times 10^9$ CFU of $\chi3339$ (wild type). Three mice were sacrificed for each time point. The results are given as geometric means±standard deviations.

This invention is predicated on the discovery that certain mutations can render a microbe avirulent without substantially affecting its immunogenicity. More specifically, this invention relates to microbial vaccines in which the microbe carries the deletion (open triangle or delta) mutations $\Delta$cya and/or $\Delta$crp eliminating the ability to synthesize adenylate cyclase (ATP pyrophosphate lyase (cyclizing) EC 4.6.1.1) and the cyclic AMP receptor protein (CRP), respectively.

Cyclic-3'5'-AMP (cAMP) and the cyclic AMP receptor protein are necessary for the transcription of a large number of genes and operons concerned with the transport and breakdown of a large number of catabolites. Evidence has been provided that shows that systems used for transporting fuel/carbon sources are all under positive control by cAMP, as are several amino acid permeases. In addition to its very important role in catabolism, the cAMP concentration in cells also influences lysogenization by temperate phages, synthesis of fimbriae, synthesis of flagella and synthesis of at least one outer membrane protein. Although cAMP is present in mammalian cells, the concentrations present in macrophages and other cells in which Salmonella can invade and multiply are below the concentration of 0.1 to 1.0 mM cAMP necessary to allow $\Delta$cya mutants to exhibit a wild-type phenotype in vitro. Furthermore, the inclusion of the $\Delta$crp mutation would essentially abolish any benefit that could accrue from uptake of cAMP in vitro or in vivo by such $\Delta$cya mutants.

Introduction of the mutations into cya and crp of S. typhi can be accomplished by use of transposons, to transfer the mutations from other Salmonella strains into S. typhi. Transposons can be added to a bacterial chromosome at many points. The characteristics of transposon insertion and deletion have been reviewed in Kleckner et al. (1977), J. Mol. Biol. 116:125. For example, the transposon Tn10, which confers resistance to tetracycline (and sensitivity to fusaric acid) can be used to create $\Delta$cya and $\Delta$crp mutations in a variety of bacterial species, including, for example, E. coli and S. typhimurium. Methods for the creation and detection of these mutants in S. typhimurium are described in EPO Pub. No. 315,682, and a method is also provided in the Examples, infra. Utilizing Tn10, these mutations can be transposed into various isolates of S. typhi, preferably those which are highly pathogenic. Examples of the transfer of the Δcya and Δcrp mutations from *S. typhimurium* into wild type *S. typhi* strains are shown in the Examples, infra.

Once rendered avirulent by the introduction of the Δcya and/or Δcrp mutations, the microbes can serve as the immunogenic component of a vaccine to induce immunity against the microbe.

In another embodiment of the invention, the *S. typhi* which are cva mutants and/or crp mutants are further mutated, preferably by a deletion, in a gene adjacent to the crp gene which governs virulence of Salmonella. Mutation in this gene, the cdt gene, diminishes the ability of the bacteria to effectively colonize deep tissues, e.g., the spleen. When a plasmid having the $crp^+$ gene is placed in a strain with the Δ(crp-cdt), it retains its avirulence and immunogenicity thus having a phenotype similar to cya and crp mutants. Mutants with the Δ(crp-cdt) mutation containing a $crp^+$ gene on a plasmid retain the normal ability to colonize the intestinal tract and GALT, but have a diminished ability to colonize deeper tissues. In the Examples, the original Δ(crp-cdt) mutation as isolated in χ3622 also deleted the argD and cysG genes imposing requirements for arginine and cysteine for growth; this mutant allele has been named Δ(crp-cysG)-10. A second mutant containing a shorter deletion was isolated that did not impose an arginine requirement; it is present in χ3931 and has been named Δ(crp-cysG)-14. Mutations in cdt in *S. typhi* can be either created directly, or can be introduced via transposition from *S. typhimurium* strains such as those shown in the Examples. In addition, the cdt mutation can be created in other strains of Salmonella using techniques known in the art, and phenotypic selection using the characteristics described herein; alternatively, the Δcdt mutation can be transposed from the *S. typhimurium* described in the Examples into other strains of Salmonella using techniques of transposon mutagenesis which are known in the art.

In still another embodiment of the invention, the avirulent derivative of a pathogenic *S. typhi* can be used as a carrier bacteria to deliver selected antigens to the GALT, for example to the Peyer's patches of the ileum. Salmonella are known to home to the Peyer's patches (Carter, P. B. and F. M. Collins, *J. Exo. Med.* 139:1189 (1974)). *S. typhimurium-E. coli* hybrids have also been shown to colonize Peyer's patches in mice (Hohmann, A. W., et al., *Infect. and immun.* 22:763 (1978)). If these carrier bacteria contain and express a recombinant gene from a pathogenic organism, antibodies against the antigenic gene product produced from the pathogen will be induced. With the advent of recombinant DNA techniques, it now becomes possible to develop totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable to eliciting an autoimmune state.

Methods of preparing organisms, particularly Salmonella, which can function as carrier bacteria are discussed in WO 89/03427 (published 20 Apr., 1989), and in U.S. Ser. No. 07/251,304, filed 3 Oct., 1988, which is commonly owned. Both of these references are incorporated herein by reference. Generally, the Salmonella are treated to cause a mutation in a chromosomal gene which encodes an enzyme that is essential for cell survival, wherein this enzyme catalyzes a step in the biosynthesis of an essential cell wall structural component. An extrachromosomal genetic element, for example, a recombinant vector, is introduced into the mutant cell. This genetic element contains a first recombinant gene which encodes an enzyme which is a functional replacement for the native enzyme, but the first recombinant gene cannot replace the defective chromosomal gene. The first recombinant gene is structurally linked to a second recombinant gene encoding a desired product, which is to be expressed in the carrier microorganism. Loss of the first recombinant gene causes the cells to lyse when the cells are in an environment where a product due to the expression of the first recombinant gene is absent.

A number of genes which encode enzymes essential for cell survival, which catalyze a step in the biosynthesis of an essential cell wall structural component, are known in the art, for e.g., aspartate semialdehyde dehydrogenase (Asd), which is encoded by the asd gene. A method for introducing a deletion mutation in the asd gene of *S. typhi* utilizing transposon mutagenesis is shown in the Examples. Also shown in the Examples, is the construction of a genetic element which carries the functional replacement for the asd gene, linked to a gene encoding an antigen which is to be expressed in the avirulent carrier *S. typhi.*

It is apparent that the present invention has wide applicability to the development of effective vaccines against bacterial, fungal, parasite or viral disease agents where local immunity is important and might be a first line of defense. Some examples are vaccines for the control of pneumonic plague caused by *Yersinia pestis*, of gonorrhea caused by *Neisseria gonorrhoeae*, of syphilis caused by *Treponema pallidum*, and of venereal diseases as well as eye infections caused by *Chlamydia trachomatis*. Species of Streptococci from both group A and group B, such as those species that cause sore throat or heart disease, *Neisseria meningitidis, Mycoplasma pneumoniae, Haemophilus influenzae, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholerae*, Shigella species, and *Legionella pneumophila* are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovirus, Adenovirus, Herpesvirus, Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment, when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal or invertebrate comprising a live avirulent derivative of a pathogenic microbe said derivative being incapable of producing functional adenylate cyclase and cAMP receptor protein while being capable of expressing a recombinant gene derived from an organism that is a pathogen of or that produces an allergen of said animal.

In yet another embodiment the avirulent microbes of this invention may be used as vectors for the synthesis of various host proteins. Because the avirulent microbes of this invention are able to traverse a variety of immunocompetent structures including GALT, mesenteric lymph nodes and spleen after introduction into the host, such microbes may be used to target a variety of immunoregulatory products. Accordingly, one or more genes encoding immunoregulatory proteins or peptides may be recombinantly introduced into the avirulent microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, and interleukins.

Still another embodiment of the subject invention is the use of the avirulent microbes contemplated herein to deliver and produce pharmacologically active products that might stimulate or suppress various physiological functions (i.e., growth rate, blood pressure, etc.).

In an embodiment which contemplates all of the above, a subject of the invention is avirulent strains of *S. typhi*, which carry mutations in the cya and/or crp genes.

The creation of cya and/or crp mutants of *S. typhi*, including those which also contain mutations in cdt, and/or the mutations in carrier microorganisms can also be accomplished using other techniques known in the art. These techniques include for example, standard techniques of mutagenesis and/or the use of recombinant DNA techniques. The desired mutants are then selected on the basis of phenotypic characteristics, some of which are described infra., in the Examples, and which are shown in Table 8. Each of the terms in these embodiments of the invention is analyzed in the following discussion.

By immunogenic agent is meant an agent used to stimulate the immune system of a living organism, so that one or more functions of the immune system are increased and directed towards the immunogenic agent. Immunogenic agents include vaccines. Immunogenic agents can be used in the production of antibodies, both isolated polyclonal antibodies and monoclonal antibodies, using techniques known in the art.

By vaccine is meant an agent used to stimulate the immune system of a living organism so that protection against future harm is provided. Immunization refers to the process of inducing a continuing high level of antibody and/or cellular immune response in which T-lymphocytes can either kill the pathogen and/or activate other cells (e.g., phagocytes) to do so in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Barrett, James, T., *Textbook of Immunology*: Fourth Edition, C. V. Mosby Co., St. Louis, Mo. (1983), the entire of which is herein incorporated by reference.

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies. Thus, all vertebrates are capable of responding to vaccines. Although vaccines are most commonly given to mammals, such as humans or dogs (rabies vaccine), vaccines for commercially raised vertebrates of other classes, such as the fishes and birds if of the nature described herein, are within the scope of the present invention.

An invertebrate is any member of the Animal Kingdom, excluding the vertebrates. Such animals constitute the Division Invertebrata and have no backbone or spinal column. This classification includes all animals except fishes, amphibians, reptiles, birds and mammals. Many invertebrates are capable of illiciting a primitive immune response to antigenic stimulation and are susceptible to the same microorganisms which infect vertebrates and which are disclosed herein in accordance with this invention. Exemplary of such invertebrates are shellfish and molluses and other related animals. Although the use of vaccines in the protection of invertebrate animals have hitherto before not been well documented, one skilled in the art will recognize the applicability of the subject invention to said invertebrates by use of their primitive immune systems. For example, and in accordance with this invention, the susceptibility of shellfish to infection by Salmonella will allow the introduction of avirulent strains of Salmonella species and thereby provide potential for the primitive immune system to respond. Therefore, it is within the scope of this invention, the use of an avirulent derivative of a pathogenic microbe, that is capable of infecting an invertebrate, to stimulate a response from an immune system present in said invertebrate against a pathogen.

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

One embodiment of the invention is the use of an avirulent derivative of a pathogenic microbe that attaches to, invades and persists in the GALT or BALT as a carrier of the gene product which is used for stimulating antibody response against a pathogen or allergen. Avirulent does not mean that a microbe of that genus or species cannot ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second in such a manner that reproduction of the second organism gives rise to descendents containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus, a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of an RNA molecule, polypeptide or other biological molecule by the biochemical mechanisms of the cell in which the gene is located. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

In order for a vaccine to be effective in producing antibodies, the antigenic material must be released in such a way that the antibody-producing mechanism of the vaccinated animal can come into play. Therefore, the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, are possible.

When the avirulent microbe is used as a carrier microbe, and once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell. In this way, it is possible to use a viable microbe that will persist in the vaccinated animal, for example in its Peyer's patches, and continue to produce antigen, thereby continually inducing antibody formation. A preferred gene product under these circumstances is a product that is transferred through the cell membrane into the external environment or a product that becomes attached to or embedded in the external membrane so that all or part of the gene product is exposed to the environment. Typical of this latter type of gene product are antigens normally found on the surface of the organism against which protection is desired. If these antigens are transported to the cell surface in a normal manner, antibody formation against the antigens will be enhanced.

The use of pathogens to deliver antigens from other pathogens to the GALT or BALT would be inappropriate if it were not for the fact that such pathogens can be rendered avirulent while retaining ability to colonize Peyer's patches or the BALT.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages. Further discussion of tolerance induction is given in the Barrett textbook previously cited. Lastly, the host organism itself can serve as a source of genetic material when immunoregulatory genes or genes for other pharmacologically active substances are being expressed by the vectors.

Administration of a live vaccine of the type disclosed above to an animal may be by any known or standard technique. These include oral ingestion, gastric intubation, or broncho-nasal-ocular spraying. All of these methods allow the live vaccine to easily reach the GALT or BALT cells and induce antibody formation and are the preferred methods of administration. Other methods of administration, such as intravenous injection, that allow the carrier microbe to reach the animal's blood stream may be acceptable. Intravenous, intramuscular or intramammary injection are also acceptable with other embodiments of the invention, as is described later.

Since preferred methods of administration are oral ingestion, aerosol spray and gastric intubation, preferred carrier microbes are those that belong to species that attach to, invade and persist in any of the lymphoepithelial structures of the intestines or of the bronchii of the animal being vaccinated. These strains are preferred to be avirulent derivatives of enteropathogenic strains produced by genetic manipulation of enteropathogenic strains. Strains that attach to, invade and persist in Peyer's patches and thus directly stimulate production of IgA are most preferred. In animals these include specific strains of Salmonella, and Salmonella-E. coli hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a part of the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific basepair sites. Following ligation to plasmid, phage or cosmid vectors to form recombinant molecules the recombinant molecules may be transferred into a host cell by various means such as transformation (uptake of naked DNA from the external environment, which can be artificially induced by the presence of various chemical agents, such as calcium ions), including electroporation. Other methods such as transduction are also suitable, wherein the recombinant DNA is packaged within a phage such as transducing phage or cosmid vectors. Once the recombinant DNA is in the carrier cell, it may continue to exist as a separate piece (generally true of complete transmitted plasmids) or it may insert into the host cell chromosome and be reproduced with the chromosome during cell division.

Although transferring genetic material is relatively straightforward, predicting which transfers will result in expressed genes is not yet possible. This selection process, however, does not present any difficulty to the present invention. Since the host microbe must express the transferred gene and thereby produce an antigen, a "shotgun" approach works well. Antibodies are first produced against the desired antigen, for example, fragments of cell membranes from pathogenic microbes, by standard techniques. DNA from the organism that is the source of the antigen is cleaved into multiple fragments by endonucleases, and the fragments are inserted randomly into carrier microbes that express antigens from the pathogen can be easily identified by their reaction with antibody against pathogen antigens. Antigen-expressing microbes can be selected and cloned to give the desired recombinant organism. Shotgun cloning is well known and is described in detail in Maniatis, T., et al., *Molecular Cloning, Second Edition*, Cold Spring Harbor Laboratories (1989), which is herein incorporated by reference. The techniques of gene transfer are not considered to be part of this invention, and any method capable of producing recombinant organisms comprising genes from an organism that are expressed in avirulent microbes will suffice.

In cases where the species normally exchange genetic information more classical methods of gene transfer may be employed such as conjugation, transformation or transduction.

Derivatives of avirulent microbes are also contemplated to be within the scope of this invention. By derivative is meant sexually or asexually derived progeny and mutants of the avirulent strains including single or multiple base substitutions, deletions, insertions or inversions which retain the inability to produce functional adenylate cyclase and/or cAMP receptor protein and/or the expression of the cdt gene, with or without naturally occurring virulence plasmids. For example, strains such as 4062 and 4064 carry the gyrA mutation conferring nalidixic acid resistance which has been used herein as a convenient marker to follow strains through the animal following oral inoculation. However, drug resistance is not a desirable attribute for strains to be used as vaccines. Thus, the gyrA mutation can be easily removed by transducing the wild-type gyrA+ (conferring sensitivity to nalidixic acid) gene into strains by selecting for inheritance of a closely linked Tn10 and then removing Tn10 by transduction with a phage lysate propagated on the parent strain carrying the gyrA$^-$ allele with selection for fusaric acid resistance.

The dosages required will vary with the antigenicity of the gene product and need only be an amount sufficient to induce an immune response typical of existing vaccines. Routine experimentation will easily establish the required amount. Multiple dosages are used as needed to provide the desired level of protection.

The pharmaceutical carrier or excipient in which the vaccine is suspended or dissolved may be any solvent or solid or encapsulated in a material that is non-toxic to the inoculated animal and compatible with the carrier organism or antigenic gene product. Suitable pharmaceutical carriers are known in the art, and for example, include liquid carriers, such as normal saline and other non-toxic salts at or near physiological concentrations, and solid carriers, such as talc or sucrose and which can also be incorporated into feed for farm animals. Adjuvants may be added to enhance the antigenicity if desired. Wheri used for administering via the bronchial tubes, the vaccine is preferably presented in the form of an aerosol. Suitable pharmaceutical carriers and adjuvants and the preparation of dosage forms are described in, for example, Remington's Pharmaceutical Sciences, 17th Edition, (Gennaro, Ed., Mack Publishing Co., Easton, Pa., 1985).

Immunization with a pathogen-derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen-derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific examples which are provided herein for purposes of illustration only and are not intended to be limiting unless otherwise specified.

EXAMPLES

Example 1

This example describes the isolation of avirulent microbes by the introduction of deletion mutations affecting CAMP synthesis and utilization and the identification of strains with mutations conferring stability of phenotype, complete avirulence and high immunogenicity.

Bacterial strains. The *Escherichia coli* and *Salmonella typhimurium* strains used are listed in Table 1.A. and B. They were maintained as frozen cultures suspended in 1% Bacto-peptone containing 5% glycerol and fast-frozen in dry ice-ethanol for storage in duplicate at −70° C. and also suspended in 1% Bacto-peptone containing 50% glycerol for storage at −20° C. for routine use.

Media. Complex media for routine cultivation were L broth (Lennox, *Virology* 1:190–206, (1965)) and Luria broth (Luria and Burrous, *J. Bacteriol.* 74:461–476 (1957)). Difco agar was added to Luria broth at 1.2% for base agar and 0.65% for soft agar. Penassay agar was used for routine enumeration of bacteria. Fermentation was evaluated by supplementing MacConkey base agar or Eosin methylene blue agar (Curtiss, *Genetics* 58:9–54 (1968)) with 1% final concentration of an appropriate carbohydrate.

Synthetic media were minimal liquid (ML) and minimal agar (MA) supplemented with nutrients at optimal levels as previously described (Curtiss, *J. Bacteriol.* 89:28–40, (1965)). Buffered saline with gelatin (BSG) (Curtiss, 1965 supra) was used routinely as a diluent.

Transduction. Bacteriophage P22HTint was routinely used for transduction using standard methods (Davis et al., "A Man. for Gepet. Eng.-Adv.Bacterial Genetics". Cold Spring Harbor Laboratory, Cold Spring Harbor, N.Y., (1979) ). An overnight culture of the donor strain was diluted 1:20 into prewarmed Luria broth, grown for 60 minutes with shaking at 37° C. and then infected with P22HTint at a multiplicity of 0.01. The infection mixture was shaken overnight for approximately 15 h, chloroform added and allowed to shake an additional 10 in at 37° C., and the suspension centrifuged (Sorvall RC5C, SS-34 rotor, 7,000 rpm, 10 min) to remove bacterial debris. The supernatant fluid containing the phage (ca. $10^{10}$/ml) was stored at 4° C. over chloroform. Tetracycline to a concentration of 12.5 μg/ml was used to select for transduction of TnlO insertions and Tn10-induced mutations.

Fusaric acid selection for loss of Tn10. The media and methods described by Maloy and Nunn (*J. Bacteriol.* 145:1110–1112, (1981)) were used. Strains with Tn10-induced mutations were grown overnight in L broth containing 12.5 mg tetracycline/ml at 37° C. to approximately $5\times10^8$ CFU/ml. Cultures were then diluted 1:40 into prewarmed L broth without tetracycline and aerated at 37° C. to a titer of about $2\times10^9$ CFU/ml. Suitable numbers of cells (i.e. $10^7$–$10^8$) diluted in BSG were plated on fusaric acid-containing medium and incubated 48 h at 37° C. Fusaric acid-resistant isolates were purified on the same selective medium. Single isolates were picked, grown and tested for tetracycline sensitivity on Penassay agar with and without 12.5 μg tetracycline/ml.

Mice. Female BALB/c mice (6 to 8 weeks old) (Sasco, Omaha, Nebr.) were used for infectivity and/or immunization experiments. Animals were held for one week in a quarantined room prior to being used in experiments. Experimental mice were placed in Nalgene filter-covered cages with wire floors. Food and water were given ad libitum. The animal room was maintained at 22°–23° C. with a period of 12 h illumination.

Animal infectivity. The virulence of *S. typhimurium* strains was determined following peroral (p.o.) or intraperitoneal (i.p.) inoculation. Bacteria for inoculation in mice were grown overnight as standing cultures at 37° C. in L broth. These cultures were diluted 1:50 into prewarmed L broth and aerated at 37° C. for approximately 4 h to an $OD_{600}$ of about 0.8–1.0. The cells were concentrated 50-fold by centrifugation in a GSA rotor at 7,000 rpm for 10 min at 4° C. in a Sorvall RC5C centrifuge followed by suspension in BSG. Suitable dilutions were plated on Penassay agar for titer determination and on MacConkey agar with 1% maltose to verify the Cya/Crp phenotype. For all p.o. inoculations with *S. typhimurium*, mice were deprived of food and water for 4 h prior to infection. They were then given 30 ml of 10% (w/v) sodium bicarbonate using a Pipetman P200 10–15 min prior to p.o. feeding of 20 μl of *S. typhimurium* suspended in BSG using a Pipetman P20. Food and water were returned 30 min after oral inoculation. Morbidity and mortality of mice were observed over a 30-day period. Intraperitoneal inoculation of unfasted BALB/c mice was performed using a 26-gauge ⅜" needle to deliver 100 μl of *S. typhimurium* bacterial suspension diluted in BSG. Morbidity and mortality of mice were observed over a 30-day period.

Evaluation of protective immunity. In initial experiments, any mice that survived infection with any *S. typhimurium* mutant strain for 30 days were challenged on day 31 with $10^3$–$10^4$ times the $LD_{50}$ dose of the wild-type mouse-virulent *S. typhimurium* parent strain by the p.o. route. Subsequently, groups of mice were perorally immunized with various doses of a virulent mutants and then challenged with various doses of virulent wild-type parent cells at various times after the initial immunization. Morbidity and mortality were observed throughout the experiment and for a least 30 days after challenge with the wild-type parent.

Isolation of *S. typhimurium* strains with Δcya-12 and Δcrp-11 mutations. The wild-type, mouse-passaged virulent *S. typhimurium* SL1344 strain χ3339 were genetically modified as described below, using classical genetic methods similar to those described in Curtiss and Kelly (1987). The strategy consisted of transducing the original crp-773::Tn10 mutation from PP1037 and the original cya::Tn10 mutation from PP1002 into the highly virulent and invasive *S. typhimurium* SL1344 strain χ3339 and screening numerous independent fusaric acid resistant, tetracycline sensitive deletion mutants for complete avirulence and highest immunogenicity in mice, as well as for greatest genotypic stability.

Transduction of the Tn10 insertions in the crp and cya genes was facilitated by first making a high-titer bacteriophage P22HTint lysate on the *S. typhimurium* strain PP1037 containing the crn-773::Tn10 mutation and another lysate on the *S. typhimurium strain PP*1002 containing the cya::Tn10 mutation. The resulting P22HTint lysates were subsequently used to infect the recipient S. tvyhimurium X3339 at a multiplicity of 0.3 to transduce it to tetracycline resistance with screening for a maltose-negative phenotype. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., a tetracycline-resistant, maltose-negative colony resulting from the P22HTint (PP1037)→χ3339 infection and a tetracycline-resistant, maltose-negative colony resulting from the P22HTint (PP1002)→χ3339 infection were picked into 0.5 ml BSG and streaked onto the same selective media. The resulting χ3339 derivatives were designated χ3604 (cya::Tn10) and χ3605 (crp-773::Tn10) (Table 1.A.).

TABLE 1

Bacterial strains

| Strain number | Relevant genotype | Derivation |
|---|---|---|
| **A. *E. coli*** | | |
| CA8445 | pSD110 (crp$^+$ Ap$^r$)/ Δcrp-45 Δcya-06 | Schroeder and Dobrogosz, J. Bacteriol. 167:616–622 (1986). |
| χ6060 | F' traD36 proA$^+$ proB$^+$ lacI$^q$ ΔlacZM15::Tn5/ araD139 Δ(ara, leu)-7697 ΔlacX74 ΔphoA20 galE galK recA rpsE argE$_{am}$ rpoB thi | Goldschmidt, Thoren-Gordon and Curtiss, J. Bacteriol. 172:3988–4001 (1990). |
| **B. *S. typhimurium*** | | |
| 798 | wild-type prototroph | Received from R. Wood, NADC, Ames, IA, as a swine isolate. |
| #30875 | wild-type prototroph | Received from P. McDonough, Cornell Univ. NY as a horse isolate. |
| DU8802 | zhc-1431::Tn10 | Sanderson and Roth, Microbiol. Rev. 42:485–532 (1988) |
| PP1002 | cya::Tn10 | Postma, Keizer and Koolwijk, J. Bacteriol. 168:1107–1111 (1986). |
| PP1037 | crp-773::Tn10 | Postma, Keizer and Koolwijk, supra. |
| SGSC452 | leu hsdLT galE trpD2 rpsL120 metE551 metA22 hsdSA hsdSB ilv | Sanderson and Roth, 1988 supra. |
| TT172 | cysG::Tn10 | Sanderson and Roth, 1986 supra. |
| TT2104 | zid-62::Tn10 | Sanderson and Roth, supra. |
| χ3000 | LT2-Z prototroph | Gulig and Curtiss, Infect. Immun. 55:2891–2901 (1987). |
| χ3140 | SR-11 wild-type prototroph | Gulig and Curtiss, 1987 supra. |
| χ3306 | SR-11 gyrA1816 | Gulig and Curtiss, 1987 supra. |
| χ3385 | LT-2 hsdL6 galE496 trpB2 flaA66 his-6165 rpsL120 xyl-404 metE551 metA22 lamB$^+$ (*E. coli*) Δ[zja::Tn10] hsdSA29 val | Tinge and Curtiss, J. Bacteriol. 172: in press (1990). |
| χ3339 | SL1344 wild type hisG rpsL | Smith et al., Am. J. Vet. Res. 43:59–66 (1984). |
| χ3520 | ΔasdA1 zhf-4::Tn10 | ATCC53681; Asd$^-$ tetracycline-resistant derivative of χ3000. |
| χ3604 | hisG rpsL cya::Tn10 | P22HTint(PP1002) → χ3339 with selection for tetracycline resistance (Mal$^-$). |
| χ3605 | hisG rpsL crp-773::Tn10 | P22HTint(PP1037) → χ3339 with selection for tetracycline resistance (Mal$^-$). |
| χ3615 | hisG rpsL Δcya-12 | Fusaric acid-resistant, tetracycline-sensitive Mal$^-$ derivative of χ3604. |
| χ3622 | hisG rpsL Δ[crp-cysG]-10 | Fusaric acid-resistant tetracycline-sensitive Mal$^-$ Cys$^-$ Arg$^-$ derivative of χ3605. |
| χ3623 | hisG rpsL Δcrp-11 | Fusaric acid-resistant, tetracycline-sensitive Mal$^-$ derivative of χ3605. |
| χ3670 | pSD110$^+$ hsdL6 galE496 trpB2 flaA66 his-6165 rpsL120 xyl-404 metE551 metA22 lamB$^+$ (*E. coli*) Δ[zja::Tn10] hsdSA29 val | χ3385 transformed with pSD110 from CA8445 with selection for ampicillin resistance, Mal$^+$. |
| χ3706 | pSD110$^+$ hisG rpsL Δ[crp-cysG]-10 | χ3622 transformed with pSD110 from with CA8445 selection for ampicillin resistance, Mal$^+$. |
| χ3711 | hisG rpsL Δcya-12 zid-62::Tn10 | P22HTint(χ3738) → χ3615 with selection for tetracycline resistance, Mal$^-$. |
| χ3712 | hisG rpsL Δcrp-10 zhc-1431::Tn10 | P22HTint(χ3741) → χ3622 with selection for tetracycline resistance, Mal$^-$, (Cys$^-$, Arg$^-$). |
| χ3722 | pSD110$^+$ hisG rpsL Δ[crp-cysG]-10 Δcya-12 zid-62::Tn10 | P22HTint(χ3711) → χ3706 with selection for tetracycline resistance (Mal$^-$). |
| χ3723 | pSD110$^+$ hisG rpsL Δ(crp-cysG)-10 Δcya-12 Δ[zid-62::Tn10] | Fusaric acid-resistant, tetracycline-sensitive, ampicillin-resistant, Mal$^-$, Cys$^-$, Arg$^-$ derivative of χ3723. |
| χ3724 | hisG rpsL Δ[crp-cysG]-10 Δcya-12 Δ[zid-62::Tn10] | Ampicillin-sensitive derivative of χ3723; pSD110 cured by serial passage in L broth at 37° C. |
| χ3730 | leu hsdLT galE trpD2 rpsL120 ΔasdA1 Δ(zhf-4::Tn10) metE551 metA22 hsdSA hsdSB ilv | Asd$^-$ Tc$^s$ derivative of SGSC452. |
| χ3731 | pSD110$^+$ hisG rpsL crp-773::Tn10 | Spleen isolate of χ3706 from BALB/c mouse. |
| χ3738 | zid-62::Tn10 | P22HTint(TT2104) → χ3000 with selection for tetracycline resistance. |
| χ3741 | zhc-1431::Tn10 | P22HTint(DU8802) → χ3000 with selection for tetracycline resistance. |
| χ3761 | UK-1 wild-type prototroph | ATCC68169; Spleen isolate of #30875 from White leghorn chick. |
| χ3773 | hisG rpsL Δcrp-11 zhc-1431::Tn10 | P22HTint([χ3741) → χ3623 with selection for tetracycline resistance (Mal$^-$). |
| χ3774 | pSD110$^+$ hisG rpsL Δcrp-11 | χ3623 transformed with pSD110 from CA8445 with selection for ampicillin resistance, Mal$^+$. |
| χ3777 | Δ[crp-cysG]-10 zhc-1431::Tn10 | P22HTint(χ3712) → 798 with selection for tetracycline resistance, Mal$^-$, (Cys$^-$, Arg$^-$). |
| χ3779 | Δ[crp-cysG]-10 Δ[zhc-1431::Tn10] | P22HTint(χ3712) → #30875 with selection for tetracycline resistance, Mal$^-$, (Cys$^-$, Arg$^-$). |
| χ3784 | Δ[crp-cysG]-10 Δ[zhc-1431::Tn10] | Fusaric acid-resistant, tetracycline-sensitive, Mal$^-$, Cys$^-$, Arg$^-$ derivative of χ3779. |
| χ3806 | Δ[crp-cysG]-10 Δ[zhc-1431::Tn10] | Fusaric acid-resistant, tetracycline-sensitive, ampicillin-resistant, Mal$^-$, Cys$^-$, Arg$^-$ derivative of χ3777. |
| χ3825 | Δcrp-11 zhc-1431::Tn10 | P22HTint(χ3773) → 798 with selection for tetracycline resistance, Mal$^-$. |
| χ3828 | Δcrp-11 zhc-1431::Tn10 | P22HTint(χ3773) → UK-1 with selection for tetracycline resistance, Mal$^-$. |
| χ3876 | Δcrp-11 Δ[zhc-1431::Tn10] | Fusaric acid-resistant, tetracycline-sensitive, Mal$^-$ derivative of χ3825. |
| χ3901 | pSD110$^+$ Δ[crp-cysG]-10 Δ[zhc-1431::Tn10] | P22HTint(χ3670) → χ3806 with selection for ampicillin resistance, Mal$^+$, (Cys$^-$, Arg$^-$). |
| χ3902 | pSD110$^+$ Δ[crp-cysG]-10 Δ[zhc-1431::Tn10] Δcya-12 zid-62::Tn10 | P22HTint(χ3711) → χ3901 with selection for tetracycline resistance, Mal$^-$, (Cys$^-$, Arg$^-$). |
| χ3910 | hisG rpsL cysG::Tn10 | P22HTint(TT172) → χ3339 with selection for tetracycline resistance, Cys$^-$. |
| χ3931 | hisG rpsL Δ[crp-cysG]-14 | Fusaric acid-resistant, tetracycline-sensitive, Mal$^-$, Cys$^-$, (Arg$^+$) derivative of χ3910. |
| χ3936 | hisG rpsL Δcrp-11 Δcya-12 zid-62::Tn10 | P22HTint(χ3711) → χ3774 with selection for tetracycline resistance, Mal$^-$. |

TABLE 1-continued

Bacterial strains

| Strain number | Relevant genotype | Derivation |
|---|---|---|
| χ3937 | hisG rpsL Δcrp-11 Δcya-12 zid-62::Tn10 | Fusaric acid-resistant, tetracycline sensitive, Mal⁻ derivative of χ3936. |
| χ3938 | pSD110⁺ Δcrp-11 Δ[zhc-1431::Tn10] | P22HTint(χ3670) → χ3876 with selection for ampicillin resistance, Mal⁺. |
| χ3939 | hisG rpsL Δcrp-11 Δcya-12 Δ[zid-62::Tn10] | Ampicillin-sensitive derivative of χ3937; pSD110 cured by serial passage in L broth at 37° C. |
| χ3945 | pSD110⁺ Δ[crp-cysG]-10 Δ[zhc-1431::Tn10] | P22HTint(χ3670) → χ3784 with selection for ampicillin resistance, Mal⁺. |
| χ3954 | Δcrp-11 Δ[zhc-1431::Tn10] | Fusaric acid-resistant, tetracycline-sensitive, Mal⁻ derivative of χ3828 |
| χ3955 | hisG rpsL Δ[crp-cysG]-14 | P22HTint(χ3670) → χ3931 with selection for ampicillin resistance, Mal⁺, (Cys⁻, Arg⁺). |
| χ3956 | pSD110⁺ Δ[crp-cysG]-10 Δ[zhc-1431::Tn10] Δcya-12 zid-61::Tn10 | P22HTint(χ3711) → χ3945 with selection for tetracycline resistance, Mal⁻, Cys⁻, Arg⁻. |
| χ3957 | pSD110⁺ Δ[crp-cysG]-10 Δ[zhc-1431::Tn10] Δcya-12 Δ[zid-61::Tn-10] | Fusaric acid-resistant, tetracycline-sensitive, Mal⁻, Cys⁻, Arg⁻ derivative of χ3956. |
| χ3958 | Δ[crp-cysG]-10 Δ[zhc-1431::Tn10] Δcya-12 Δ[zid-61::Tn10] | Ampicillin-sensitive derivative of χ3957; pSD110 cured by serial passage in L broth at 37° C. |
| χ3961 | pSD110⁺ Δcrp-11 Δ[zhc-1431::Tn10] | P22HTint(χ3670) → χ3954 with selection for ampicillin resistance, Mal⁺. |
| χ3962 | pSD110⁺ Δcrp-11 Δ[zhc-1431::Tn10] Δcya-12 zid-62::Tn10 | P22HTint(χ3711) → χ3961 with selection for tetracycline resistance, Mal⁻. |
| χ3978 | pSD110⁺ Δcrp-11 Δ[zhc-1431::Tn10] Δcya-12 zid-62::Tn10 | P22HTint(χ3711) → χ3938 with selection for tetracycline resistance, Mal⁻. |
| χ3985 | Δcya-12 Δ[zid-62::Tn10] Δcrp-11 Δ[zhc-1431::Tn10] | ATCC68166; Fusaric acid-resistant, tetracycline-sensitive, Mal⁻ derivative of χ3962 cured of pSD110. |
| χ4038 | Δcya-12 Δ[zid-62::Tn10] Δ[crp-cysG]-10 Δ[zhc-1431::Tn10] | Fusaric acid-resistant tetracycline-sensitive Mal⁻, Cys⁻, Arg⁻ derivative of χ3902 cured of pSD110. |
| χ4039 | Δcya-12 Δ[zid-62::Tn10] Δ[crp-cysG]-10 Δ[zhc-1431::Tn10] | Fusaric acid-resistant, tetracycline-sensitive Mal⁻ derivative of χ3978 cured of pSD110. |
| χ4063 | SR-11 arg::Tn10 | P22HTint(Tn10 library) → χ3306 with selection for tetracycline resistance, Arg⁻. |
| χ4071 | SR-11 arg::Tn10 | P22HTint(Tn10 library) → χ3306 with selection for tetracycline resistance, Arg⁻. |
| χ4246 | Δ[crp-cysG]-10 zhc-1431::Tn10 | P22HTint(χ3712) → 798 with selection for tetracycline resistance, Mal⁻, (Cys⁻ Arg⁻). |
| χ4247 | pSD110⁺ Δ[crp-cysG]-10 zhc-1431::Tn10 | P22HTint(χ3670) → χ4246 with selection for ampicillin resistance, Mal⁺, (Cys⁻ Arg⁻). |
| χ4248 | Δ[crp-cysG]-10 zhc-1431::Tn10 | P22HTint(χ3712) → ATCC68169 (UK-1) with selection for tetracycline resistance, Mal⁻, (Cys⁻ Arg⁻). |
| χ4262 | PSD110⁺ Δ[crp-cysG]-10 zhc-1431::Tn10 | P22HTint(χ3670) → χ4248 with selection for ampicillin resistance, Mal⁺, (Cys⁻ Arg⁻). |

C. *S. typhi*

| Strain number | Relevant genotype | Derivation |
|---|---|---|
| Ty2 | Type E1 Cys⁻ Trp⁻ wild type | Louis Baron, Walter Reed Army Institute of Research |
| ISP1820 | Type 46 Cys⁻ Trp⁻ wild type | Center for Vaccine Development, Baltimore, MD; 1983 isolate from Chilean patient. |
| ISP2822 | Type E1 Cys⁻ Trp⁻ wild type | Center for Vaccine Development, Baltimore, MD; 1983 isolate from Chilean patient. |
| χ3791 | Δ[crp-cysG]-10 zhc-1431::Tn10 | P22HTint(χ3712) → ISP2822 with selection for tetracycline resistance (Mal⁻, Cys⁻, Arg⁻, Vi⁺). |
| χ3792 | Δ[crp-cysG]-10 zhc-1431::Tn10 | P22HTint(χ3712) → Ty2 with selection for tetracycline resistance (Mal⁻, Cys⁻, Arg⁻ Vi⁺) |
| χ3802 | Δ[crp-cysG]-10 Δ[zhc-1431::Tn10] | Fusaric acid-resistant, tetracycline-sensitive Mal⁻ derivative of χ3791 (Vi⁺). |
| χ3803 | Δ[crp-cysG]-10 Δ[zhc-1431::Tn10] | Fusaric acid-resistant, tetracycline-sensitive Mal⁻ derivative of χ3792 (Vi⁺). |
| χ3824 | pSD110⁺ Δ[crp-cysG]-10 Δ[zhc-1431::Tn10] | χ3803 electro-transformed with pSD110 from χ3670 with selection for ampicillin resistance (Mal⁺, Cys⁻, Arg⁻, Vi⁺). |
| χ3845 | pSD110⁺ Δ[crp-cysG]-10 Δ[zhc-1431::Tn10] | χ3802 electro-transformed with pSD110 from χ3670 with selection for ampicillin resistance (Mal⁺, Cys⁻, Arg⁻, Vi⁺). |
| χ3852 | Δcrp-11 zhc-1431::Tn10 | P22HTint(Δ3773) → ISP2822 with selection for tetracycline resistance (Mal⁻, Vi⁺). |
| χ3853 | Δcrp-11 zhc-1431::Tn10 | P22HTint(χ3773) → Ty2 with selection for tetracycline resistance (Mal⁻, Vi⁺). |
| χ3877 | Δcrp-11 Δ[zhc-1431::Tn10] | Fusaric acid-resistant, tetracycline-sensitive Mal⁻ derivative of χ3852 (VI⁺). |
| χ3878 | Δcrp-11 Δ[zhc-1431::Tn10] | Fusaric acid-resistant, tetracycline-sensitive Mal⁻ derivative of χ3853 (Vi⁺). |
| χ3879 | PSD110⁺ Δcrp-11 Δ[zhc-1431::Tn10] | P22HTint(χ3670) → Δ3877 with selection for ampicillin resistance (Mal⁺, Vi⁺). |
| χ3880 | pSD110⁺ Δcrp-11 Δ[zhc-1431::Tn10] | P22HTint(χ3670) → χ3878 with selection for ampicillin resistance (Mal⁺, Vi⁺). |
| χ3919 | pSD110⁺ Δ[crp-cysG]-10 Δ[zhc-1431::Tn10] Δcya-12 zid-62::Tn10 | P22HTint(χ3711) → χ3824 with selection for tetracycline resistance (Mal⁻, Vi⁺). |
| χ3920 | pSD110⁺ Δ[crp-cysG]-10 Δ[zhc-1431::Tn10] Δcya-12 zid-62::Tn10 | P22HTint(χ3711) → χ3845 with selection for tetracycline resistance (Mal⁻, Vi⁺). |
| χ3921 | pSD110⁺ Δcrp-11 Δ[zhc-1431::Tn10] Δcya-12 zid-62::Tn10 | P22HTint(χ3711) → χ3879 with selection for tetracycline resistance (Mal⁻, Vi⁺). |
| χ3922 | pSD110⁺ Δcrp-11 Δ[zhc-1431::Tn10] Δcya-12 zid-62::Tn10 | P22HTint(χ3711) → χ3880 with selection for tetracycline resistance (Mal⁻, Vi⁺). |
| χ3924 | Δ[crp-cysG]-10 Δ[zhc-1431::Tn10] Δcya-12 Δ[zid-62::Tn10] | Fusaric acid-resistant, tetracycline-sensitive Mal⁻ derivative of χ3919 cured of pSD110 (Vi⁺). |
| χ3925 | Δ[crp-cysG]-10 Δ[zhc-1431::Tn10] | Fusaric acid-resistant, tetracycline-sensitive Mal⁻ derivative of χ3920 |

TABLE 1-continued

Bacterial strains

| Strain number | Relevant genotype | Derivation |
|---|---|---|
| | Δcya-12<br>Δ[zid-62::Tn10] | cured of pSD110 (Vi+). |
| χ3926 | Δcrp-11<br>Δ[zhc-1431::Tn10]<br>Δcya-12<br>Δ[zid-62::Tn10] | Fusaric acid-resistant, tetracycline-sensitive Mal− derivative of χ3921 cured of pSD110 (Vi+). |
| χ3927 | Δcrp-11<br>Δ[zhc-1431::Tn10]<br>Δcya-12<br>Δ[zid-62::Tn10] | Fusaric acid-resistant, tetracycline-sensitive Mal−, derivative of χ3922 cured of PSD110 (Vi+). |
| χ3940 | Δ[crp-cysG]-10<br>Δ[zhc-1431::Tn10]<br>Δcya-12<br>Δ[zid-62::Tn10] | Flagella-positive, motile derivative of χ3925 (Vi+). |
| χ4073 | Δ[crp-cysG]-10<br>Δ[zhc-1431::Tn10]<br>Δcya-12<br>Δ[zid-62::Tn10] | Flagella-positive, motile derivative of χ3924 (Vi+). |
| χ4296 | Δcrp-11<br>Δ[zhc-1431::Tn10]<br>Δcya-12<br>Δ[zid-62::Tn10]<br>ΔasdA1<br>zhf-4::Tn-10 | P22HTint(χ3520) → χ3927 with selection for tetracycline resistance and screening for Asd−, Mal−, Vi+. |
| χ4297 | Δcrp-11<br>Δ[zhc-1431::Tn10]<br>Δcya-12<br>Δ[zid-62::Tn10]<br>ΔasdA1<br>Δ[zhf-4::Tn10] | Fusaric acid-resistant, tetracycline-sensitive, Asd−, Mal− derivative of χ4296 (Vi+). |
| χ4298 | Δcrp-11<br>zhc-1431::Tn10 | P22HTint(χ3773) → ISP1820 with selection for tetracycline resistance (Mal−, Vi+). |
| χ4299 | Δcrp-11<br>Δ[zhc-1431::Tn10] | Fusaric acid-resistant, tetracycline-sensitive Mal− derivative of χ4298 (Vi+). |
| χ4300 | pSD110+<br>Δcrp-11<br>Δ[zhc-1431::Tn10] | P22HTint(χ3670) → Δ4299 with selection for ampicillin resistance (Mal+, Vi+). |
| χ4316 | pSD110+<br>Δcrp-11<br>Δ[zhc-1431::Tn10]<br>Δcya-12<br>zid-62::Tn10 | P22HTint(χ3670) → χ4300 with selection for tetracycline resistance (Mal−, Vi+) |
| χ4322 | Δcrp-11<br>Δ[zhc-1431::Tn10]<br>Δcya-12<br>Δ[zid-62::Tn10] | Fusaric acid-resistant, tetracycline-sensitive Mal− derivative of χ4316 cured of pSD110 (Vi+). |
| χ4323 | Δcrp-11<br>Δ[zhc-1431::Tn10]<br>Δcya-12<br>Δ[zid-62::Tn10] | Flagella-positive, motile derivative of χ4322 (Vi+) |
| χ4324 | Δ[crp-cysG]-10<br>zhc-1431::Tn10 | P22HTint(χ3712) → ISP1820 with selection for tetracycline resistance (Mal−, Cys−, Arg−, Vi+). |
| χ4325 | Δ[crp-cysG]-10<br>Δ[zhc-1431::Tn10] | Fusaric acid-resistant, tetracyline-sensitive Mal− derivative of χ4324 (Vi+). |
| χ4331 | pSD110+<br>Δ[crp-cysG]-10<br>Δ[zhc-1431::Tn10] | P22HTint(χ3670) → χ4325 with selection for ampicillin resistance (Mal+, Vi+). |
| χ4340 | pSD110+<br>Δ[crp-cysG]-10<br>Δ[zhc-1431::Tn10]<br>Δcya-12<br>zid-62::Tn10 | P22HTint(χ3711) → χ4331 with selection for tetracycline resistance Mal−, Vi+). |
| χ4345 | Δ[crp-cysG]-10<br>Δ[zhc-1431::Tn10]<br>Δcya-12<br>Δ[zid-62::Tn10] | Fusaric acid-resistant, tetracycline-sensitive Mal− derivative of χ4340 cured of pSD110 (Vi+). |
| χ4346 | Δ[crp-cysG]-10<br>Δ[zhc-1431::Tn10]<br>Δcya-12<br>Δ[zid-62::Tn10] | Flagella-positive, motile derivative of χ4345 (Vi+). |
| χ4416 | Δ[crp-cysG]-10<br>Δ[zhc-1431::Tn10]<br>ΔasdA1 zhf-4::Tn10<br>Δcya-12<br>Δ[zid-62::Tn10] | P22HTint(χ3520) → χ4346 with selection for tetracycline resistance and screening for Asd−, Mal−, Vi+. |
| χ4417 | [Δcrp-cysG]-10<br>Δ[zhc-1431::Tn10]<br>ΔasdA1 zhf-4::Tn10<br>Δcya-12<br>Δ[zid-62::Tn10] | Fusaric acid-resistant, tetracyline-sensitive Asd−, Mal− derivative of χ4416 (Vi+). |
| χ4434 | Δcrp-11<br>Δ[zhc-1431::Tn10]<br>ΔasdA1<br>zhf-4::Tn10<br>Δcya-12<br>Δ[zid-62::Tn10] | P22HTint(χ3520) → χ4323 with selection for tetracycline resistance and screening for Mal−, Asd−, Vi+. |
| χ4435 | Δcrp-11<br>Δ[zhc-1431::Tn10]<br>ΔasdA1<br>Δ[zhf-4::Tn10]<br>Δcya-12<br>Δ[zid-62::Tn10] | Fusaric acid-resistant, tetracycline-sensitive Mal− derivative of χ4434 (Vi+). |

Strains χ3604 and χ3605 were grown in L broth+12.5 μg tetracycline/ml and 100 μl samples of each strain diluted 1:10 into buffered saline with gelatin (BSG) were spread onto 10 plates of fusaric acid-containing (FA) media (Maloy and Nunn, 1981). The plates were incubated approximately 36 h at 37° C. Five fusaric acid-resistant colonies from each plate were picked into 0.5 ml BSG and purified on FA media. Purified fusaric acid-resistant colonies were picked into L broth and grown at 37° C. to turbidity and checked for loss of Tn10 (tetracycline sensitivity). One tetracycline-sensitive derivative was selected from each of the ten platings on FA media and characterized for complete LPS (by P22HTint sensitivity), auxotrophy or prototrophy, stability of the gene deletion, and reversion to tetracycline resistance. This procedure resulted in ten independently isolated Δcya mutants from χ3604 and ten independently isolated Δcrp mutants from χ3605.

Genetic stability of avirulent mutants. Strains to be orally administered as live vaccines must have complete stability with regard to both their avirule bce and their immunogenic attributes. When 50-fold concentrated cultures and various dilutions (~$10^9$, $10^7$, $10^5$, $10^3$ CFU/plate) of each of the ten independent Δcya mutants and each of the ten independent Δcrp mutants were plated on minimal agar media (supplemented with 22 μg cysteine/ml and 22 μg arginine/ml) containing 0.5% maltose, melibiose, xylose, glycerol, or rhamnose that should not support their growth, revertants and mutants were not detected. One set of duplicate plates were UV-irradiated (5 joules/meter$^2$/sec) and incubated at 37° C. in the dark. The other set of plates was incubated at 37° C. with illumination. Revertants and mutants were not detected after a 48 h growth period. An investigation was also conducted as to whether tetracycline-resistant revertants/mutants could be recovered from the fusaric acid resistant Δcya and Δcrp mutants at frequencies higher than could be observed for the tetracycline-sensitive wild-type parental strain. In all cases, such tetracycline-resistant revertants/mutants were not observed.

Virulence and immunogenicity of Δcrp and Δcya mutants. The resulting ten Δcrp and ten Δcya mutants were screened in BALB/c mice by peroral inoculation to determine the lowest virulence and disease symptomology as revealed by the appearance of the coat (scruffy versus smooth), appetite, and activity (high or low). Five mice per group were p.o. inoculated with ~$10^9$ CFU of each of the independent cya or crp deletion mutants. Animals were scored based on the above criteria and on day 30 of the experiment the survivors were challenged with $10^8$ CFU of the wild-type virulent parent strain χ3339. In three of the twenty groups infected with the cya or crp deletion mutants, five of five mice survived the initial infection with the Δcya-12, Δcrp-11 and Δcrp-10 mutants and were also completely protected against $10^4$ $LD_{50}$s of the wild-type challenge. One group in particular, the Δcrp-10 mutant, was unequalled in avirulence, immunogenicity and stability. After repeating these experiments, mice never appeared affected by any dose given p.o. or i.p. of the Δcrp-10 mutant (see Example 3, Table 6).

Properties of selected mutant strains. χ3615, χ3622 and χ3623 with the Δcya-12, Δcrp-10 and Δcrp-11 mutations, respectively, were judged to be least virulent, highly immunogenic and extremely stable phenotypically and genotypically. Data on the phenotypic properties of these strains is given in Table 2. Table 3 presents data on the avirulence and immunogenicity of these strains in comparison to results with the virulent wild-type parent χ3339 and strains χ3604 and χ3605 with the cya::Tn10 and crp-773::Tn10 mutations, respectively. In addition to requiring histidine, which is due to the hisG mutation in the parental χ3339, the Δcrp-10 mutation imposed on χ3622 requirements for the amino acids arginine and cysteine. The bases for this observation and further analysis of the properties of the Δcrp-10 mutation are given in Example 3.

cAMP synthesis and utilization and the characterization of strains with two deletion mutations for stability of phenotype, complete avirulence and high immunogenicity.

Bacterial strains. The *Escherichia coli* and *Salmonella typhimurium* strains used are listed in Table 1.A. and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Animal infectivity and evaluation of protective immunity. The virulence and immunogenicity of *S. typhimurium* strains were determined as described in Example 1.

Construction of *S. typhimurium* strains with Δcya-12 and Δcrp-11 deletion mutations. The best vaccine strains in terms of efficacy are likely to result from the attenuation of highly virulent strains that display significant colonizing ability and invasiveness. The criteria for selection of these highly pathogenic *S. typhimurium* wild-type strains such as SL1344 (χ3339), UK-1 (χ3761) and 798 included low $LD_{50}$ values (see Table 4) in mouse virulence assays, antibiotic sensitivity, possession of the virulence plasmid, ease of genetic manipulation (bacteriophage P22HTint or P1 sensitivity, transformability and ease of receiving mobilized plasmids), and colicin sensitivity.

The wild-type, virulent *S. typhimurium* strains SL1344 (χ3339), 798 and UK-1 (χ3761) were genetically modified as described below, using classical genetic methods similar to those described in Curtiss and Kelly (1987). The strategy

TABLE 2

Phenotypic characteristics of *S. typhimurium* Δcya and Δcrp strains

| Strain and genotype | P22[a] | Carbohydrate fermentation and use[b] | | | | | | | | Auxotrophy | | |
|---|---|---|---|---|---|---|---|---|---|---|---|---|
| | | Mal | Mtl | Ino | Srl | Rha | Mel | Gal | Glc | His | Arg | Cys |
| χ3339 wild type | S | + | + | + | + | + | + | + | + | − | + | + |
| χ3615 Δcya-12 | S | − | − | − | − | − | − | +/− | + | − | + | + |
| χ3622 Δcrp-10 | S | − | − | − | − | − | − | +/− | + | − | − | − |
| χ3623 Δcrp-11 | S | − | − | − | − | − | − | +/− | + | − | + | + |

[a]Bacteriophage P22HTintS = Sensitive; R = Resistant
[b]Fermentation on MacConkey Base agar media and API 20E and growth on MA + 0.5% of carbon source.

TABLE 3

Virulence and immunogenicity of *S. typhimurium* cya::Tn10, crp::Tn10 Δcya-12, Δcrp-10 and Δcrp-11 mutants in BALB/c mice

| Strain number | Relevant genotype | P.O. immunization | | Wild-type P.O. challenge | |
|---|---|---|---|---|---|
| | | Dose (CFU) | Survival live/total | Dose (CFU) | Survival live/total |
| χ3339 | wild type | — | — | 6.0 × $10^4$ | 2/5 |
| χ3604 | cya::Tn10 | 6.2 × $10^8$ | 5/5 | 8.8 × $10^8$ | 4/5 |
| χ3605 | crp-773::Tn10 | 6.8 × $10^8$ | 5/5 | 8.8 × $10^8$ | 5/5 |
| χ3615 | Δcya-12 | 2.2 × $10^9$ | 5/5 | 3.2 × $10^8$ | 5/5 |
| χ3622 | Δcrp-10 | 1.5 × $10^9$ | 5/5 | 3.2 × $10^8$ | 5/5 |
| χ3623 | Δcrp-11 | 4.6 × $10^8$ | 5/5 | 8.8 × $10^8$ | 5/5 |

Example 2

This example describes the construction of avirulent microbes by the introduction of deletion mutations affecting consists of mobilizing deletions of crp and cya genes that have been isolated and characterized in *S. typhimurium* SL1344 (as described in Example 1) by placing the transposon Tn10 (encoding tetracycline resistance) nearby the Δcya-12 or Δcrp-11 mutation and transducing the linked traits into the highly virulent *S. typhimurium* strains UK-1 χ3761, 798 and SL1344 χ3339 via P22HTint-mediated transduction with selection for tetracycline resistance and screening for a maltose-negative phenotype. The zhc-1431::Tn10 linked to Δcrp-11 and zid-62::Tn10 linked to Δcya-12 were used for this purpose. Neither insertion alone affects the virulence of *S. typhimurium*.

Transduction of the gene deletions with the linked transposon was facilitated by first making a high-titer bacteriophage P22HTint lysate on the *S. typhimurium* strain X3773 containing the Δcrp-11 and zhc-1431::Tn10 mutations and another lysate on the *S. typhimurium* strain χ3711 containing the Δcya-12 and zid-62::Tn10 mutations. The resulting P22HTint lysates were then used to transduce the genetic traits into the wild-type recipient strains X3339, 798 and χ3761.

P22HTint propagated on S. typhimurium χ3773 (Δcrp-11 zhc-1431::Tn10) was used to transduce the virulent strains to tetracycline resistance with screening for Mal⁻. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., tetracycline resistant Mal⁻ transductants were picked and purified onto the same medium. The resulting 798 derivative was designated χ3825 and the UK-1 derivative was designated χ3828. Strains χ3773, χ3825 and χ3828 have the genotype Δcrp-11 zhc-1431::Tn10 (Table 1.B.). These strains were grown in L broth+12.5 μg tetracycline/ml and each were diluted 1:10 into buffered saline with gelatin (BSG), 100 μl of each were spread onto fusaric acid-containing (FA) media (Maloy and Nunn, 1981) and the plates were incubated approximately 36 h at 37° C. Fusaric acid-resistant colonies of each strain were picked into 0.5 ml BSG and purified onto FA media. Purified fusaric acid-resistant colonies were picked into L broth and grown at 37° C. to turbidity and checked for loss of Tn10 (tetracycline sensitivity), presence of complete LPS and auxotrophy. The new strains were designated χ3876 (798) and χ3954 (UK-1) which both have the genotype Δcrp-11 Δ[zhc-1431::Tn10] and χ3623 (SL1344 Δcrp-11 was originally isolated as described in Example 1) (Table 1.B.).

Since the phenotype of Cya⁻ and Crp⁻ mutants are the same (Mal⁻, Stl⁻, Mtl⁻, etc.), the plasmid, pSD110, carrying the cloned crp⁺ gene and conferring ampicillin resistance (Schroeder and Dobrogosz, J. Bacteriol 167:616–622 (1986)), was used to temporarily complement the Δcrp mutation in the chromosome enabling the identification of the Δcya mutation when introduced via transduction. L broth grown cultures of χ3623, χ3876 and χ3954 were transduced with P22HTint propagated on S. typhimurium χ3670, which contains the plasmid pSD110 (Table 1.B.). Selection was made on MacConkey agar+1% maltose+100 μg ampicillin/ml. After 26 h, an ampicillin-resistant, Mal⁺ colony of each strain was picked and purified on MacConkey agar+1% maltose agar+100 μg ampicillin/ml and designated χ3938 (798) and χ3961 (UK-1) which both have the genotype Δcrp-11 Δ[zhc-1431::Tn10] pSD110⁺ and χ3774 (SL1344) which has the genotype Δcrp-11 pSD110⁺.

Strains χ3774, χ3938 and χ3961 were grown in L broth+ 100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+ 100 μg ampicillin/ml+12.5 μg tetracycline/ml. Ampicillin-resistant (pSD110⁺), tetracycline-resistant (zid-62::Tn10), Mal⁻ (Δcya) colonies were picked and purified on MacConkey agar+1% maltose+100 μg ampicillin/ml+12.5 μg tetracycline/ml. Purified colonies were picked into L broth, grown to turbidity and the strains checked for complete LPS and auxotrophy. The resulting strains were designated χ3978 (798) and χ3962 (UK-1) which both have the genotype Δcrp-11 Δ[zhc-1431::Tn10] pSD110⁺Δcya-12 zid-62::Tn10 and χ3936 (SL1344) which has the genotype Δcrp-11 pSD110⁺Δcya-12 zid-62::Tn10. Cultures of χ3936, χ3978 and χ3962 were grown in L broth+100 μg ampicillin/ml+ 12.5 μg tetracycline/ml to turbidity, diluted 1:10 into BSG, and 100 μl samples of each culture spread onto fusaric acid-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10 (tetracycline sensitivity), complete LPS and auxotrophy. The pSD110 plasmid was usually lost spontaneously from the strains during this process to result in ampicillin sensitivity, except for the SL1344 derivative which involved two steps to eliminate pSD110. The final strains were designated χ4039 (798) and χ3985 (UK-1) which both have the genotype Δcrp-11 Δ[zhc-1431::Tn10] Δcya-12 Δ[zid-62::Tn10] and χ3939 (SL1344) which has the genotype Δcrp-11 Δcya-12 Δ(zid-62::Tn10) (Table 1.B.).

Genotypic and phenotypic stability of avirulent mutants. Methods for determining stability of genetic traits are as described in Example 1. All genotypic and phenotypic traits due to the Δcya Δcrp mutations were completely stable except motility. Although synthesis of functional flagella and display of motility is dependent on wild-type cya and crp gene functions, a suppressor mutation in the cfs (constitutive flagellar synthesis) gene can easily be selected to cause flagella synthesis and motility to be independent of cya and crp gene functions. In S. typhimurium Δcya Δcrp strains, motile variants were readily selected during the strain construction process. Since immunity to flagellar antigens may be protective, motile variants of all vaccine strains were selected.

S. typhimurium group B O-antigen synthesis was confirmed by slide agglutination with antisera (Difco Laboratories, Detroit, Mich.) and by P22HTint bacteriophage sensitivity by the Luria soft agar overlay technique.

Fermentation of sugars and growth on various carbon sources of the double mutant strains were identical to strains with only Δcya or Δcrp as listed in Table 2. The phenotypes were as expected based on published reports of the requirement for cyclic AMP and the cyclic AMP receptor protein for catabolic activities.

At each step in the construction following selection of a fusaric acid-resistant tetracycline-sensitive derivative, an investigation as to whether tetracycline-resistant revertants/ mutants could be recovered at frequencies higher than could be observed for the parental tetracycline-sensitive wild-type strain was conducted. In all cases, such tetracycline-resistant revertants/mutants were not observed.

Virulence of mutant strains for mice. Preliminary information on virulence of S. typhimurium mutant strains was obtained by infecting individual mice with $10^8$ mutant cells perorally and recording morbidity and mortality. Table 4 presents data on morbidity and mortality of mice infected perorally with the S. typhimurium wild-type parent strains, and the Δcya-12 Δcrp-11 derivatives χ3985 and χ4039.

TABLE 4

Virulence of S. typhimurium Δcya-12, Δcrp-11, Δcya-12, and Δcrp-11 Strains After Inoculation of BALB/c Mice with S. typhimurium Δcya-12 and/or Δcrp-11 Strains

| Strain Number | Relevant Genotype | Route of Inoculation | Inoculating Dose (CFU) | Survival live/Total | Health[a] | Approx. wild-type $LD_{50}$ | Wild-type Origin |
|---|---|---|---|---|---|---|---|
| S. typhimurium | | | | | | | |
| χ3615 | Δcya-12 | PO | $2 \times 10^9$ | 5/5 | healthy | $6 \times 10^4$ | mouse |
| χ3623 | Δcrp-11 | PO | $5 \times 10^8$ | 5/5 | healthy | $6 \times 10^4$ | mouse |
| χ3985 | Δcya-12 Δcrp-11 | PO | $2 \times 10^9$ | 8/10 | moderate | $1 \times 10^5$ | horse |
| χ4039 | Δcya-12 Δcrp-11 | PO | $1 \times 10^9$ | 10/10 | healthy | $1 \times 10^5$ | pig |
| S. typhi | | | | | | | |
| χ3926 | Δcya-12 Δcrp-11 | IP[b] | $2 \times 10^3$ | 4/6 | healthy | ~29 | human |
| χ3927 | Δcya-12 Δcrp-11 | IP | $3 \times 10^3$ | 2/4 | healthy | <20 | human |

[a]Healthy — no noticeable signs of disease; moderate — moderately ill; ill — noticeably ill
[b]IP — cells delivered in 0.5 ml 5% hog gastric mucin.

Effectiveness of immunization with avirulent mutants. Table 5 presents data on the ability of the S. typhimurium Δcya Δcrp mutants χ3985 and χ4039 to induce immunity to subsequent peroral challenge with $10^4$ times the $LD_{50}$ doses of fully virulent wild-type S. typhimurium cells. Under these high-dose challenges, many of the mice displayed moderate illness with decreased food consumption except mice immunized with χ4039 which remained healthy and ate and grew normally.

TABLE 5

Effectiveness of Immunization with Avirulent S. typhimurium Δcya-12 and/or Δcrp-11 Mutants in Protecting Against Challenge with Wild-type Virulent Parent Strains

| Strain number | Relevant Genotype | Dose (CFU) of Immunizing Strain | Dose (CFU) of Wild-type Challenge Strain | Survival live/total |
|---|---|---|---|---|
| χ3615 | Δcya-12 | $2 \times 10^9$ | $3 \times 10^8$ | 5/5 |
| χ3623 | Δcrp-11 | $5 \times 10^8$ | $3 \times 10^8$ | 5/5 |
| χ3985 | Δcya-12 Δcrp-11 | $2 \times 10^9$ | $7 \times 10^8$ | 8/8 |
| χ4039 | Δcya-12 Δcrp-11 | $1 \times 10^9$ | $6 \times 10^8$ | 10/10 |

Example 3

This Example demonstrates the isolation of an avirulent microbe that possesses a deletion mutation encompassing the crp gene and an adjacent gene which also governs virulence of Salmonella.

Bacterial strains. The *Escherichia coli* and *Salmonella typhimurium* strains used are listed in Table 1A and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Animal infectivity and evaluation of protective immunity. The virulence and immunogenicity of *S. typhimurium* strains were determined as described in Example 1.

Isolation of *S. typhimurium* strain with the Δcrp-10 mutation. As described in Example 1, one of ten Δcrp mutations isolated in χ3605 conferred auxotrophy for arginine (due to deletion of argD) and cysteine (due to deletion of cysG). The mutation in the *S. typhimurium* SL1344 strain χ3622 was originally referred to as Δcrp-10 but is now designated Δ[crp-cysG]-10 because of the auxotrophy for cysteine. A group of five BALB/c mice orally infected with $10^9$ χ3622 cells remained healthy and was totally unaffected (Table 3). Furthermore, these mice gained high-level immunity to oral challenge with $10^8$ parental χ3339 cells (Table 3).

A series of strains was constructed to independently evaluate each of the phenotypic characteristics of χ3622. The plasmid, pSD110, carrying the cloned crp$^+$ gene and conferring ampicillin resistance (Schroeder and Dobrogosz, *J. Bacteriol.* 167:616–622 (1986)), was used to complement the Δcrp mutation in the chromosome. An L broth culture of χ3622 was transduced with P22HTint propagated on *S. typhimurium* χ3670, which contains the plasmid pSD110. Selection was made on MacConkey agar+1% maltose+100 μg ampicillin/ml. After 26 h, an ampicillin-resistant, Mal$^+$ colony was picked and purified on MacConkey agar+1% maltose agar+100 μg ampicillin/ml and designated χ3706. χ3706 was administered perorally to mice and reisolated from the spleen. The animal-passaged strain was designated χ3737. Two other crp mutants, χ3605(crp-773::Tn10) and χ3623 (Δcrp-11) that do not confer the Arg$^-$ or Cys$^-$ auxotrophic traits were also complemented with the pSD110 plasmid by transduction and designated χ3731 and χ3774, respectively. *S. typhimurium* strains independently carrying cysG and arg mutations were constructed and designated χ3910 (cysG::Tn10), χ4063 and χ4071 (arg::Tn10).

Two other highly pathogenic *S. typhimurium* strains were selected for attenuation by introduction of the Δcrp-10 mutation. χ3761 (UK-1) and 798 are virulent, invasive strains isolated from a moribund horse and pig, respectively, with $LD_{50}$s in mice of approximately $1 \times 10^5$ CFU. Transduction of Δcrp-10 with the linked transposon zhc-1431::Tn10 was facilitated by first making a high-titer bacteriophage P22HTint lysate on the *S. typhimurium* strain χ3712 (see Table 1.B.). The phage lysate was then used to transduce the genetic traits into the wild-type recipient strains χ3761 and 798. Tetracycline-resistant colonies were selected and screened for the Mal$^-$, Arg$^-$ and Cys$^-$ phenotypes and the resulting 798 derivative designated χ4246 and the χ3761 (UK-1) derivative designated χ4248 (Table 1).

The crp mutation was complemented by introducing pSD110, carrying the crp$^+$ wild-type allele, into χ4246 and χ4248. L broth grown cultures of χ4246 and χ4248 were transduced with P22HTint propagated on *S. typhimurium*χ3670, which contains the plasmid pSD110 (Table 1). Selection was made on MacConkey agar+1% maltose+100 µg ampicillin/ml+12.5 µg tetracycline/ml. After 26 h, an ampicillin, Mal⁺ colony of each strain was picked and purified on the same medium and designated χ4247 (798) and χ4262 (UK-1) which both have the genotype pSD110⁺/Δcrp-10 zhc-1431::Tn10.

Virulence of the *S. typhimurium* χ3622, χ3731, χ3737, χ3774, χ3910, χ4063 and χ4071. Table 6 presents data on morbidity and mortality of mice infected perorally with the *S. typhimurium* strains χ3622, χ3731, χ3737, χ3774, χ3910, χ4063 and χ4071. Strain χ3737 was completely avirulent for mice that received $10^4$ times the $LD_{50}$ dose for the wild-type χ3339 parent strain. Mice never appeared ill throughout the 30-day observation period. As a control for this experiment, the crp-773::Tn10 mutation in χ3605 was complemented by pSD110 to the wild-type Crp⁺ phenotype (χ3731) and mice were infected and died. Doses around $1 \times 10^5$ CFU killed 4 of 5 mice p.o. inoculated with χ3731 and χ3774 (pSD110$^{+/\Delta Crp-11}$). To test the virulence of strains with the Cys⁻ and Arg⁻ phenotypes independently, strains χ3910 (cysG::Tn10), χ4063 (arg::Tn10) and χ4071 (arg::Tn10) were p.o. administered to BALB/c mice. χ3910, χ4063 and χ4071 killed mice when similar or lower doses were p.o. administered. Therefore, the avirulence associated with the Δ[crp-cysG]-10 mutation was not solely due to deletion of the crp gene and was not conferred by deletion of either the argD or cysG loci. Rather, another gene necessary for *S. typhimurium* virulence must be localized to the region of chromosome near the crp gene.

TABLE 6

Virulence of *S. typhimurium* SL1344 Δ[crp-cysG]-10, Crp⁺/(crp::Tn10 and Crp⁺/Δ[crp-cysG]-10, arg::Tn10, cysG::Tn10 mutants in BALB/c mice 30 days after peroral inoculation

| Strain number | Relevant genotype | Inoculating dose (CFU) | Survival live/total | Mean day of death[a] | Health[b] |
|---|---|---|---|---|---|
| χ3339 | wild-type | $6 \times 10^4$ | 2/5 | 7 | scruffy |
| χ3622 | Δ[crp-cysG]-10 | $6 \times 10^8$ | 5/5 | — | healthy |
| χ3731 | pSD110⁺ | $1 \times 10^5$ | 1/5 | 9 | scruffy |
| χ3737 | crp-773::Tn10 pSD110+ Δ[crp-cysG]-10 | $5 \times 10^8$ | 5/5 | – | healthy |
| χ3774 | pSD110⁺ Δcrp-11 | $3 \times 10^4$ | 3/5 | 12 | scruffy |
| χ3910 | cysG::Tn10 | $1 \times 10^7$ | 0/2 | 12 | scruffy |
| χ4063 | arg::Tn10 | $1 \times 10^9$ | 0/2 | 8 | scruffy |
| χ4071 | arg::Tn10 | $1 \times 10^9$ | 0/2 | 9 | scruffy |

[a]of animals that died
[b]healthy — no noticeable signs of disease; moderate — moderately ill; scruffy — noticeably ill.

Effectiveness of immunization with χ3622, χ3737, χ4247 and χ4262. Data on the ability of χ3622, χ3737, χ4247 and χ4262 to induce immunity to subsequent p.o. or i.p. challenge with $10^4$ times the $LD_{50}$ doses of fully virulent wild-type *S. typhimurium* cells are presented in Table 7. All mice given excessive doses of the wild-type parent strain never appeared ill throughout the 30-day duration of the experiment. Therefore the Δ[crp-cysG]-10 mutation deletes at least two genes both of which render *S. typhimurium* completely avirulent and highly immunogenic.

TABLE 7

Effectiveness of immunization with avirulent *S. typhimurium* Δ[crp-cysG]-10 mutants in protecting against challenge with wild-type virulent parent strains

| Strain number | Relevant genotype | Dose (CFU) of immunizing strain | Route of immunization | Dose (CFU) of wild-type strain | Survival live/total |
|---|---|---|---|---|---|
| χ3622 | Δ[crp-cysG]-10 | $6.2 \times 10^8$ | PO | $3.6 \times 10^8$ | 5/5 |
|  |  | $1.5 \times 10^9$ | PO | $3.2 \times 10^8$ | 5/5 |
|  |  | $4.2 \times 10^8$ | PO | $8.8 \times 10^8$ | 5/5 |
|  |  | $9.0 \times 10^6$ | IP | $1.4 \times 10^4$ | 2/2 |
|  |  | $9.0 \times 10^4$ | IP | $1.4 \times 10^4$ | 3/3 |
|  |  | $9.6 \times 10^2$ | IP | $1.4. \times 10^4$ | 3/3 |
| χ3737 | pSD110⁺ Δ[crp-cysG]-10 | $5.8 \times 10^8$ | PO | $8.4 \times 10^8$ | 5/5 |
| χ3955 | pSD110⁺ Δ[crp-cysG]-14 | $6.8 \times 10^8$ | PO | $8.4 \times 10^8$ | 2/2 |
| χ4247 | PSD110⁺ Δ[crp-cysG]-10 | $2.0 \times 10^9$ | PO | $9.8 \times 10^8$ | 2/2 |
| χ4262 | PSD110⁺ [crp-cysG]-10 | $1.5 \times 10^9$ | PO | $5.4 \times 10^8$ | 3/3 |

Isolation of *S. typhimurium* strain with the Δcrp-14 mutation. Since an imprecise excision event of crp-773::Tn10 generated the deletion of genes extending from argD through cysG, another strategy was designed to locate the position of the gene conferring avirulence in the region adjacent to crp. Twenty independent deletion mutants of χ3910 (cysG::Tn10) were selected on fusaric acid-containing medium and screened for tetracycline-sensitivity and maltose-negative phenotype. One of twenty fusaric acid-resistant derivative of χ3910 had the genotype Δ[crp-cysG]-14 and conferred auxotrophy for histidine and cysteine, but not arginine. This strain, designated χ3931, was transduced with a P22HTint lysate-grown on χ3670 to introduce pSD110 carrying the wild-type crp⁺ gene. An ampicillin-resistant, maltose-positive transductant was picked and purified on the same medium and the resulting strain was designated χ3955.

Virulence of *S. typhimurium* pSD110⁺/Δ[crp-cysG]-14 χ3955. Table 7 shows morbidity and mortality of mice infected perorally with *S. typhimurium* χ3955. Strain χ3955 was completely avirulent for mice that received approximately $10^9$ CFU. Mice never appeared ill throughout the 30-day period.

Effectiveness of immunization with χ3955. Table 7 shows the ability of χ3955 to induce immunity to subsequent p.o. challenge with $10^4$ times the $LD_{50}$ dose of fully virulent wild-type *S. typhimurium* cells. Mice given excessive doses of the parent strain never appeared ill throughout the 30-day duration of the experiment.

Colonization of intestinal tract. GALT and spleen by χ3622(Δ[crp-cysG]-10) and χ3737 (pSD110⁺ Δ[crp-cysG]-10) relative to the wild-type strain χ3339. *S. typhimurium* χ3622 and χ3737 were grown and prepared for oral inoculation of 8-week-old female BALB/c mice as described in Example 1. Animals were sacrificed 1, 3, 5 and 7 days after p.o. inoculation with $9.4 \times 10^8$ CFU (χ3622), $1.2 \times 10^9$ CFU (χ3737) or $1.1 \times 10^9$ CFU (χ3339). Three mice per group were randomly selected, euthanized and tissue samples collected. The spleen, Peyer's patches, a 10-cm section of the ileum and the small intestinal contents from each mouse were placed in polypropylene tubes with BSG, homogenized with a Brinkmann tissue homogenizer and placed on ice. Undiluted or diluted samples (100 µl) were plated directly on MacConkey agar+1% lactose+50 µg streptomycin/ml (χ3339 and χ3737) and MacConkey agar+1% maltose+50 μg streptomycin/ml (χ3622) and the plates were incubated for 26 h 37° C. Titers in the perspective tissues were determined for each time period and the geometric mean calculated for 3 mice per group at each time of sampling.

Figure 1B:
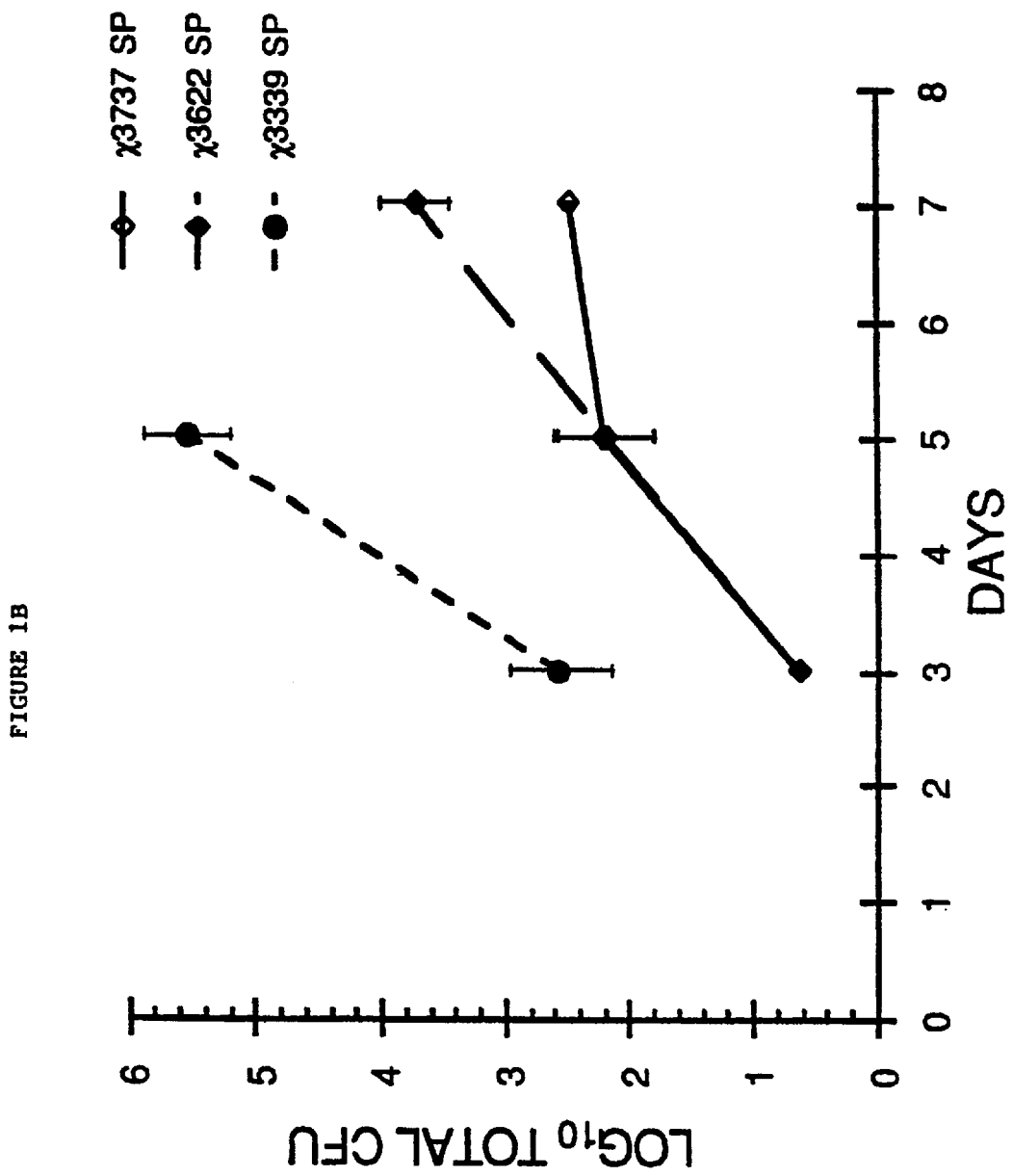

The results of this analysis are presented in FIG. 1. It is evident that the additional attenuating mutation in χ3622 and which is still manifested in the Crp⁺ (pSD110⁺) derivative χ3737 very much diminishes the ability to effectively colonize deep tissues. The responsible gene which is deleted by the Δ[crp-cysG]-10 mutation has therefore been designated cdt. The Cdt⁻ phenotype of χ3622 and χ3737 is also manifested by the absence of any splenomegaly which is observed following p.o. inoculation of mice with S. typhimurium χ3623 which has the Δcrp-11 mutation or with various other strains with combined Δcrp and Δcya mutations (Curtiss and Kelly, 1987). Strain χ3737 grew more rapidly than χ3622. The additional attenuating mutation in χ3622 does not decrease growth rate as does the crp mutation.

Based on isolation and analysis of deletion mutations for phenotypes conferred, the order of genes in the S. typhimurium chromosome is inferred to be argD crp cdt cysG.

It is evident that inclusion of the Δ[crp-cysG]-10 or Δ[crp-cysG]-14 mutations which are also Δcdt mutations would enhance the safety of live attenuated Salmonella vaccine strains while not diminishing their immunogenicity. This might be particularly important for host-adapted invasive Salmonella species such as S. typhi, S. paratyphi A (S. schottmuelleri), S. paratyphi B (S. hirshfeldii), S. paratyphi C (all infect humans), S. choleraesuis (infects swine), S. dublin (infects cattle), S. gallinarum, and S. pullorum (both infect poultry), as well as non-host specific, invasive Salmonella species such as S. typhimurium and S. enteritidis.

Example 4

This example describes the construction of avirulent microbes by the introduction of deletion mutations affecting cAMP synthesis and utilization and an adjacent gene which also governs virulence of Salmonella by affecting colonization of deep tissues and the characterization of strains with two deletion mutations for stability of phenotype, complete avirulence and high immunogenicity.

Bacterial strains. The *Escherichia coli* and *Salmonella typhimurium* strains used are listed in Table 1.A. and B. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Construction of S. typhimurium strains with Δcya-12 and Δ[crp-cysG]-10 deletion mutations. The best vaccine strains in terms of efficacy are likely to result from the attenuation of highly virulent strains that display significant colonizing ability and invasiveness. The criteria for selection of these highly pathogenic S. typhimurium wild-type strains such as SL1344 (χ3339), UK-1 (χ3761) and 798 has been described in Example 2.

The wild-type, virulent S. typhimurium strains SL1344, 798 and UK-1 were genetically modified as described below, using classical genetic methods similar to those described in Curtiss and Kelly (1987). The strategy consists of mobilizing deletions of crp and cya genes that have been isolated and characterized in S. typhimurium SL1344 (as described in Example 1) by placing the transposon Tn10 (encoding tetracycline resistance) nearby the Δcya-12 or Δ[crp-cysG]-10 mutation and transducing the linked traits into the highly virulent S. typhimurium strains UK-1 χ3761, 798 and SL1344 χ3339 via P22HTint-mediated transduction with selection for tetracycline resistance and screening for a maltose-negative phenotype. The zhc-1431::Tn10 linked to Δ[crp-cysG]-10 and zid-62::Tn10 linked to Δcya-12 were used for this purpose. Neither insertion alone affects the virulence of S. typhimurium.

Transduction of the gene deletions with the linked transposon was facilitated by first making a high-titer bacteriophage P22HTint lysate on the S. typhimurium strain χ3712 containing the Δ[crp-cysG]-10 and zhc-1431::Tn10 mutations and another lysate on the S. typhimurium strain χ3711 containing the Δcya-12 and zid-62::Tn10 mutations. The resulting P22HTint lysates were then used to transduce the genetic traits into the wild-type recipient strains χ3339, 798 and χ3761.

P22HTint propagated on S. typhimurium χ3712 (Δ[crp-cysG]-10 zhc-1431::Tn10) was used to transduce the virulent strains to tetracycline resistance with screening for Mal⁻. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., tetracycline resistant Mal⁻ transductants were picked and purified onto the same medium. The resulting 798 derivative was designated χ3777 and the UK-1 derivative was designated χ3779. Strains χ3712, χ3777 and χ3779 all have the genotype Δ[crp-cysG]-10 zhc-1431::Tn10 (Table 1.B.). χ3777 and χ3779 were grown in L broth+12.5 μg tetracycline/ml and each were diluted 1:10 into buffered saline with gelatin (BSG), 100 μl of each were spread onto fusaric acid-containing (FA) media (Maloy and Nunn, 1981) and the plates were incubated approximately 36 h at 37° C. Fusaric acid-resistant colonies of each strain were picked into 0.5 ml BSG and purified onto FA medium. Purified fusaric acid-resistant colonies were picked into L broth and grown at 37° C. to turbidity and checked for loss of Tn10 (tetracycline sensitivity), presence of complete LPS and auxotrophy. The new strains were designated χ3784 (UK-1) and χ3806 (798) which both have the genotype Δ[crp-cysG] -10 Δ[zhc-1431::Tn10]. χ3622 (SL1344 Δ[crp-cysG]-10) was originally isolated as described in Example 1) (Table 1B).

Since the phenotype of Cya⁻ and Crp⁻ mutants are the same (Mal⁻, Stl⁻, Mtl⁻, etc.), the plasmid, pSD110, carrying the cloned crp⁺ gene and conferring ampicillin resistance (Schroeder and Dobrogosz, J. Bacteriol 167:616–622( 1986)), was used to temporarily complement the Δcrp mutation in the chromosome enabling the identification of the Δcya mutation when introduced via transduction. L broth grown cultures of χ3622, χ3784 and χ3806 were transduced with P22HTint propagated on S. typhimurium χ3670, which contains the plasmid pSD110 (Table 1). Selection was made on MacConkey agar+1% maltose+100 μg ampicillin/ml. After 26 h, an ampicillin-resistant, Mal⁺ colony of each strain was picked and purified on MacConkey agar+1% maltose agar+100 μg ampicillin/ml and designated χ3901 (798) and χ3945 (UK-1) which both have the genotype Δ[crp-cysG]-10 Δ[zhc-1431::Tn10] pSD110⁺ and χ3706 (SL1344) which has the genotype Δ[crp-cysG]-10 pSD110⁺.

Strains χ3706, χ3901 and χ3945 were grown in L broth+ 100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+100 μg ampicillin/ml+12.5 pg tetracycline/ml. Ampicillin-resistant (pSD110+), tetracycline-resistant (zid-62::Tn10), Mal− (Δcya) colonies were picked and purified on MacConkey agar+1% maltose+100 μg ampicillin/ml+12.5 μg tetracycline/ml. Purified colonies were picked into L broth, grown to turbidity and the strains checked for complete LPS and auxotrophy. The resulting strains were designated χ3902 (798) and χ3956 (UK-1) which both have the genotype Δ[crp-cysG]-10 Δ[zhc-1431::Tn10] pSD110+ Δcya-12 zid-62::Tn10 and χ3722 (SL1344) which has the genotype Δ[crp-cysG]-10 pSD110+Δcya-12 zid-62::Tn10. Cultures of χ3722, χ3902 and χ3956 were grown in L broth+100 μg ampicillin/ml+12.5 μg tetracycline/ml to turbidity, diluted 1:10 into BSG, and 100 μl samples of each culture spread onto fusaric acid-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10 (tetracycline sensitivity), complete LPS and auxotrophy. The pSD110 plasmid was usually lost spontaneously from the strains during this process to result in ampicillin sensitivity, except for the SL1344 and UK-1 derivatives which involved two steps to eliminate pSD110. The final strains were designated χ3958 (UK-1) and χ4038 (798) which both have the genotype Δ[crp-cysG]-10 Δ[zhc-1431::Tn10] Δcya-12 Δ[zid-62::Tn10] and χ3724 (SL1344) which has the genotype Δ[crp-cysG]-10 Δcya-12 Δ[zid-62::Tn10] (Table 1.B.).

Genotypic and Phenotypic stability of avirulent mutants. Methods for determining stability of genetic traits are as described in Example 1. All genotypic and phenotypic traits due to the Δcya Δcrp mutations were completely stable except motility. Although synthesis of functional flagella and display of motility is dependent on wild-type cya and crp gene functions, a suppressor mutation in the cfs (constitutive flagellar synthesis) gene can easily be selected to cause flagella synthesis and motility to be independent of cya and crp gene functions. In S. typhimurium Δcya Δcrp strains, motile variants were readily selected during the strain construction process. Since immunity to flagellar antigens may be protective, motile variants of all vaccine strains were selected.

S. typhimurium group B O-antigen synthesis was confirmed by slide agglutination with antisera (Difco Laboratories, Detroit, Mich.) and by P22HTint bacteriophage sensitivity by the Luria soft agar overlay technique.

Fermentation of sugars and growth on various carbon sources of the double mutant strains were identical to strains with only Δcya or Δcrp as listed in Table 2. The phenotypes were as expected based on published reports of the requirement for cyclic AMP and the cyclic AMP receptor protein for catabolic activities.

At each step in the construction following selection of a fusaric acid-resistant tetracycline-sensitive derivative, an investigation as to whether tetracycline-resistant revertants/mutants could be recovered at frequencies higher than could be observed for the tetracycline-sensitive wild-type parental strain was conducted. In all cases, such tetracycline-resistant revertants/mutants were not observed.

Example 5

This Example describes the construction of avirulent microbes by the introduction of deletion mutations affecting cAMP synthesis and utilization and the characterization of strains with two deletion mutations for stability of phenotype and complete avirulence.

Bacterial strains. The Salmonella typhimurium and S. typhi strains used are listed in Table 1.B. and C. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Genetic stability of avirulent mutants. Methods for determining stability of genetic traits are as described in Example 1.

Mice. Female CFW-1 mice (18–20 g) (Charles River, Wilmington, Mass.) were used for all infectivity experiments. Animals were held for one week in a quarantined room prior to being used in experiments. Experimental mice were placed in Nalgene filter-covered cages with wire floors. Food and water were given ad libitum. The animal room was maintained at 22°–23° C. with a period of 12 h illumination.

Animal infectivity. The virulence of S. typhi strains was determined following intraperitoneal (i.p.) injection with hog gastric mucin. Bacteria for inoculation into mice were grown overnight as standing cultures at 37° C. in L broth. The cultures were diluted 1:50 into prewarmed L broth and aerated at 37° C. for approximately 4 h to an $OD_{600}$ of about 0.8–1.0. Suitable dilutions were plated on Penassay agar for titer determination and on MacConkey agar with 1% maltose to verify the Cya/Crp phenotype.

Intraperitoneal inoculation of unfasted CFW-1 mice was performed using a 26-gauge ⅜" needle to deliver 500 μl of S. typhi cells suspended in 15% (w/v) hog gastric mucin (Wilson lot #0347A001). The mucin suspension was prepared by autoclaving 10 min 121° F. (15 p.s.i.), neutralizing to pH 7 and adding 3 μg of ferric ammonium citrate (Sigma, St. Louis, Mo.) per ml prior to adding S. typhi cells. $LD_{50}$ values of the wild-type parents and virulence of the Δcrp-11 Δcya-12 derivatives were determined after recording morbidity and mortality data for 10 days.

Construction of S. typhi strains with cya and crp mutations. The wild-type, virulent S. typhi Ty2 (type E1), ISP1820 (type 46) and ISP2822 (type E1) strains were genetically modified as described below, using classical genetic methods similar to those described in Curtiss and Kelly (1987). ISP1820 and ISP2822 were recently isolated during a typhoid epidemic in Chile and are likely to be more invasive than the standard laboratory Ty2 strain of S. typhi. Their attenuation might therefore generate vaccine strains that would be more efficacious than those derived from Ty2. The construction strategy consists of mobilizing deletions of crp and cya genes that have been isolated and characterized in S. typhimurium SL1344 by placing the transposon Tn10 (encoding tetracycline resistance) nearby the Δcya or Δcrp mutation and transducing the linked traits into the highly virulent S. typhi Ty2, ISP1820 and ISP2822 strains via P22HTint-mediated transduction with selection for tetracycline resistance and screening for a maltose-negative phenotype. The zhc-1431::Tn10 linked to crp and zid-62::Tn10 linked to cya were used for this purpose. Neither insertion alone affects virulence of S. typhimurium.

Transduction of the gene deletions with the linked transposon was facilitated by first making a high-titer bacteriophage P22HTint lysate on the S. typhimurium strain χ3773 containing the Δcrp-11 and zhc-1431::Tn10 mutations and another lysate on the S. typhimurium strain χ3711 containing the Δcya-12 and zid-62::Tn10 mutations. The resulting P22HTint lysates were then used to infect at a multiplicity of infection of 10 to transduce the genetic traits into the recipient S. typhi Ty2, ISP1820 and ISP2822 strains.

P22HTint propagated on S. typhimurium χ3773 (Δcrp-11 zhc-1431::Tn10) was used to transduce the virulent S. typhi Ty2, ISP1820 and ISP2822 strains to tetracycline resistance with screening for Mal$^-$. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., tetracycline-resistant Mal$^-$ transductants were picked and purified onto the same medium. The resulting Ty2 derivative was designated χ3853, the ISP1820 derivative designated χ4298 and the ISP2822 derivative designated χ3852. All of these strains have the genotype Δcrp-11 zhc-1431::Tn10 (Table 1.C.). Strains χ3852, χ3853 and χ4298 were grown in L broth+12.5 μg tetracycline/ml and each were diluted 1:10 into buffered saline with gelatin (BSG), 100 μl of each were spread onto fusaric acid-containing (FA) media (Maloy and Nunn, 1981) and the plates were incubated approximately 36 h at 37° C. Fusaric acid-resistant colonies of each strain were picked into 0.5 ml BSG and purified onto FA medium. Purified fusaric acid-resistant colonies were picked into L broth and grown at 37° C. to turbidity and checked for loss of Tn10 (tetracycline sensitivity), presence of complete LPS and Vi antigen and auxotrophy for cysteine and tryptophan (two amino acids required by all the parent strains). The new strains were designated χ3877 (ISP2822), χ3878 (Ty2) and χ4299 (ISP1820) which all have the genotype Δcrp-11 Δ[zhc-1431::Tn10] (Table 1.C.).

Since the phenotype of Cya$^-$ and Crp$^-$ mutants are the same (Mal$^-$, Stl$^-$, Mtl$^-$, etc.), the plasmid, pSD110, carrying the cloned crp$^+$ gene conferring ampicillin resistance (Schroeder and Dobrogosz, J. Bacteriol. 167:616–622 (1986)), was used to temporarily complement the Δcrp mutation in the chromosome enabling the identification of the Δcya mutation when introduced via transduction. L broth grown cultures of χ3877, χ3878 and χ4299 were transduced with P22HTint propagated on S. typhimurium χ3670, which contains the plasmid pSD110 (Table 1.B.). Selection was made on MacConkey agar+1% maltose+100 μg ampicillin/ml. After 26 h, an ampicillin-resistant, Mal$^+$ colony of each strain was picked and purified on MacConkey agar+1% maltose agar+100 μg ampicillin/ml and designated χ3879 (ISP2822), χ3880 (Ty2) and χ4$^{300}$ (ISP1820) which all have the genotype Δcrp-11 Δ[zhc-1431::Tn10] pSD110$^+$.

Strains χ3879, χ3880 and χ4300 were grown in L broth+100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+100 μg ampicillin/ml+12.5 μg tetracycline/ml. Ampicillin-resistant (pSD110$^+$), tetracycline-resistant (zid-62::Tn10), Mal$^-$ (Δcya) colonies were picked and purified on MacConkey agar+1% maltose+100 μg ampicillin/ml+12.5 μg tetracycline/ml. Purified colonies were picked into L broth, grown to turbidity and the strains checked for complete LPS, Vi antigen and auxotrophy for cysteine and tryptophan. The resulting strains were designated χ3921 (ISP2822), χ3922 (Ty2) and χ4316 (ISP1820) which all have the genotype Δcrp-11 Δ[zhc-1431::Tn10 ] pSD110$^+$Δcya-12 zid-62::Tn10 (Table 1.C.). Cultures of χ3921, χ3922 and χ4316 were grown in L broth+100 μg ampicillin/ml+12.5 μg tetracycline/ml to turbidity, diluted 1:10 into BSG, and 100 ml samples of each culture spread onto fusaric-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10 (tetracycline sensitivity), complete LPS, Vi antigen and auxotrophy for cysteine and tryptophan. The pSD110 plasmid was usually spontaneously lost from the strains during this process to result in ampicillin sensitivity. The final strains were designated χ3926 (ISP2822), χ3927 (Ty2) and χ4322 (ISP1820) which all have the genotype Δcrp-11 Δ[zhc-1431::Tn10] Δcya-12 Δ[zid-62::Tn10] (Table 1.C.). S. typhi Vi antigen synthesis was confirmed by slide agglutination with antisera to Vi (Difco Laboratories, Detroit, Mich.) and by ViII bacteriophage sensitivity by the Luria soft agar overlay technique. Synthesis of flagella is dependent on functional cya and crp genes. However, since flagella are a potentially important antigen, motile derivatives of Δcya Δcrp S. typhi strains, due to mutation in the cfs (constitutive flagellar synthesis) gene (Silverman and Simon, J. Bacteriol. 120:1196–1203 (1974), were selected in motility agar. χ3926 and χ3927 were isolated as flagellated and motile whereas strain χ4323 was selected as a flagella-positive motile derivative of χ4222.

Table 8 lists the phenotypic properties of all the mutant strains and their parents with regard to fermentation of sugars and growth on various carbon sources, LPS profile, Vi antigen and mean generation time. The phenotypes are as expected based on published reports of the requirement for cyclic AMP and the cyclic AMP receptor protein for catabolic activities.

TABLE 8

Fermentation and growth properties of S. typhi strains

| | Phenotype | | | |
|---|---|---|---|---|
| | χ3745 | χ3926 | χ3769 | χ3927 |
| MacConkey Base Agar + 1% maltose | + | − | + | − |
| MacConkey Base Agar + 1% sorbitol | + | − | + | − |
| MacConkey Base Agar + 1% mannitol | + | − | + | − |
| MacConkey Base Agar + 1% melibiose | + | − | + | − |
| MacConkey Base Agar + 1% rhamnose | − | − | − | − |
| MacConkey Base Agar + 1% citrate | − | − | − | − |
| MacConkey Base Agar + 1% arabinose | − | − | − | − |
| MacConkey Base Agar + 1% mannose | + | + | + | − |
| MacConkey Base Agar + 1% xylose | + | − | + | − |
| MacConkey Base Agar + 1% glucose | + | + | + | + |
| Minimal agar + 0.5% glucose | + | + | + | + |
| Minimal agar + 0.5% sorbitol | + | − | + | − |
| Minimal agar + 0.5% mannitol | + | − | + | − |
| Minimal agar + 0.5% melibiose | + | − | + | − |
| Minimal agar + 0.5% rhamnose | − | − | − | − |
| Minimal agar + 0.5% citrate | − | − | − | − |
| Minimal agar + 0.5% arabinose | − | − | − | − |
| Minimal agar + 0.5% mannose | + | + | + | − |
| Minimal agar + 0.5% xylose | + | − | + | − |
| Triple Sugar Iron media − H$_2$S production | + | − | + | − |

TABLE 8-continued

Fermentation and growth properties of S. typhi strains

| | Phenotype | | | |
|---|---|---|---|---|
| | χ3745 | χ3926 | χ3769 | χ3927 |
| alkaline slant = | Lac⁻ Glu⁺ Suc⁻ | Lac⁻ Glu⁺ Suc⁻ | Lac⁻ Glu⁺ Suc⁻ | Lac⁻ Glu⁺ Suc⁻ |
| Indole fermentation assay | – | – | – | – |
| Bacteriophage sensitivity[2] | | | | |
| ViII | S | S | S | S |
| Felix-O | S | S | S | S |
| P22HTint | S | S | S | S |
| P1L4 | R | R | R | R |

TABLE 8-continued

Fermentation and growth properties of S. typhi strains

| | Phenotype | | | |
|---|---|---|---|---|
| | χ3745 | χ3926 | χ3769 | χ3927 |
| L | R | R | R | R |
| KB1 | R | R | R | R |
| LPS profile by SDS-PAGE (silver strain) | complete | complete | complete | complete |
| Motility[bd] | + | + | + | + |
| Colicin(s) production | – | – | – | – |
| MGT[c] | 21.5 | 26.2 | 24.3 | 37.1 |
| Plasmid content | none | none | none | none |
| Auxotrophy | Cys⁻ Trp⁻ | Cys⁻ Trp⁻ | Cys⁻ Trp⁻ | Cys⁻ Trp⁻ |
| MIC[d] | | | | |
| Tetracycline | 4 | 4 | <2 | 4 |
| Streptomycin | 64 | 64 | 16 | 8 |

[a]phage sensitivity was assayed by soft agar overlay technique or by transduction. S — sensitive; R = resistant.
[b]Motility determined by stabbing a loopful of a standing overnight culture into media containing 1.0% casein, 0.5% NaCl$_2$, 0.5% Difco agar, 50 μg/mg triphenyltetrazolium chloride indicator agar; incubation at 37° C. and motility recorded at 24 and 48 h.
[c]Mean Generation Time (min) = determined in Luria broth with aeration (150 rpm New Brunswick platform shaker) at 37° C.
[d]minimal inhibitory concentrations (μg/ml) of antibiotics were determined by streaking standing overnight cultures of each strain onto agar containing defined concentrations of antibiotics.

Genetic stability of avirulent mutants. Strains to be orally administered as live vaccines must have complete stability with regard to their avirulence attributes. When 50-fold concentrated cultures and various dilutions (~$10^9$, $10^7$, $10^5$, $10^3$ CFU/plate) of the Δcya Δcrp S. typhi strains were plated on minimal agar media (supplemented with required amino acids) containing 0.5% maltose, melibiose, xylose, glycerol, or rhamnose that should not support their growth, revertants and mutants were not detected. One set of duplicate plates was UV-irradiated (5 joules/meter$^2$/sec) and incubated at 37° C. in the dark. The other set of plates was incubated at 37° C. with illumination. Revertants and mutants were not detected after a 48 h growth period. An investigation was also conducted as to whether tetracycline-resistant revertants/mutants could be recovered at frequencies higher than could be observed for the parental strain. In all cases, such tetracycline-resistant revertants/mutants were not observed.

Virulence of mutant strains for mice. Table 9 contains data which show that mice survive infection with about $10^4$ times the $LD_{50}$ dose of either χ3926 or χ3927. The natural host for *S. typhi* is man. Therefore, hog gastric mucin is used as a virulence enhancer of *S. typhi* cells in mice, and thus maximizes the virulence of *S. typhi* vaccine candidates in this model system.

TABLE 9

| Virulence of *S. typhi* Δcya-12 Δcrp-11 strains after i.p. inoculation of CD-1 mice.[a] | | | | | | |
|---|---|---|---|---|---|---|
| Strain number | Relevant genotype | Route of inoculation | Inoculating dose (CPU) | Survival live/total | Approx. wild-type $LD_{50}$ | Wild-type origin |
| χ3926 | Δcya-12 Δcrp-11 | IP[b] | $2 \times 10^3$ | 4/6 | ~29 | human |
| χ3927 | Δcya-12 Δcrp-11 | IP | $3 \times 10^3$ | 2/4 | >20 | human |

IP — Cells delivered in 0.5 ml 5% hog gastric mucin.

Example 6

This Example demonstrates the construction of an avirulent microbe by the introduction of deletion mutations affecting cAMP synthesis and utilization and an adjacent gene which governs virulence of Salmonella by affecting colonization of deep tissues.

Bacterial strains. The *Salmonella typhimurium* and *S. typhi* strains used are listed in Table 1.B. and C. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Genetic stability of avirulent mutants. Methods for determining stability of genetic traits are as described in Example 1.

Construction of S. typhistrains with Δcya-12 and Δ[crp-cysG]-10 mutations. *S. typhi* is highly invasive for humans. Although *S. typhi* strains with the Δcya-12 and Δcrp-11 mutations appear to be avirulent, it would seem prudent to consider adding an additional attenuating mutation to further enhance safety without compromising immunogenicity. The properties of the Δ[crp-cysG]-10 mutation in *S. typhimurium* strains (Examples 1, 3, and 4) justify its use to render *S. typhi* avirulent and immunogenic. This mutation also deletes the cdt gene governing colonization of deep tissues by *Salmonella typhimurium* without significantly diminishing colonization of the intestinal tract and GALT.

The wild-type, virulent Ty2 (type E1), ISP1820 (type 46) and ISP2822(type E1) strains were genetically modified as described below, using classical genetic methods similar to those described in Curtiss and Kelly (1987). ISP1820 and ISP2822 were recently isolated during a typhoid epidemic in Chile and are likely to be more invasive than the standard laboratory Ty2 strain of *S. typhi*. Their attenuation might therefore generate vaccine strains that could be more efficacious than those derived from Ty2. The construction strategy consists of mobilizing deletions of crp and cya genes that have been isolated and characterized in *S. typhimurium* SL1344 (as described in Example 1) by placing the transposon Tn10 (encoding tetracycline resistance) nearby the Δcya or Δ[crp-cysG]-10 mutation and transducing the linked traits into *S. typhi* Ty2 and the highly virulent *S. typhi* ISP1820 and ISP2822 strains via P22HTint-mediated transduction with selection for tetracycline resistance and screening for a maltose-negative phenotype. The zhc-1431::Tn10 linked to [crp-cysG]-10 and zid-62::Tn10 linked to cya were used for this purpose. Neither insertion alone affects virulence of *S. typhimurium.*

Transduction of the gene deletions with the linked transposon was facilitated by first making a high-titer bacteriophage P22HTint lysate on the *S. typhimurium* strain χ3712 containing the Δ[cro-cysG]-10 and zhc-1431::Tn10 mutations and another lysate on the *S. typhimurium* strain χ3711 containing the Δcya-12 and zid-62::Tn10 mutations. The resulting P22HTint lysates were then used to transduce the genetic traits into the recipient *S. typhi* Ty2, ISP1820 and ISP2822 strains.

P22HTint propagated on *S. typhimurium* χ3712 (Δ[crp-cysG]-10 zhc-1431::Tn10) was used to transduce the virulent *S. typhi* Ty2, ISP1820 and ISP2822 strains to tetracycline resistance with screening for $Mal^-$. The phage-bacteria infection mixtures were incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26 h incubation at 37° C., tetracycline-resistant $Mal^-$ transductants were picked and purified onto the same medium. The resulting ISP2822 derivative was designated χ3791, the Ty2 derivative was designated χ3792, and the ISP1820 derivative was designated χ4324. All of these strains have the genotype Δ[crp-cysG]-10 zhc-1431::Tn10 and were auxotrophic for cysteine, tryptophan and arginine (Table 1.C.). Strains χ3791, χ3792 and χ4324 were grown in L broth+12.5 μg tetracycline/ml. Each culture was diluted 1:10 into buffered saline with gelatin (BSG), 100 μl of each was spread onto fusaric acid-containing (FA) media (Maloy and Nunn, 1981) and the plates incubated approximately 36 h at 37° C. Fusaric acid-resistant colonies of each strain were picked into 0.5 ml BSG and purified onto FA medium. Purified fusaric acid-resistant colonies were picked into L broth and grown at 37° C. to turbidity and checked for loss of Tn10 (tetracycline sensitivity), presence of complete LPS and Vi antigen and auxotrophy for cysteine, arginine and tryptophan. The new strains were designated χ3802 (ISP2822), χ3803 (Ty2) and χ4325 (ISP1820) which all have the genotype Δ[crp-cysG]-10 Δ[zhc-1431::Tn10] (Table 1.C.).

Since the phenotype of $Cya^-$ and $Crp^-/Cdt^-$ mutants are the same ($Mal^-$, $Stl^-$, $Mtl^-$, etc.), the plasmid, pSD110, carrying the cloned $crp^+$ gene and conferring ampicillin resistance (Schroeder and Dobrogosz, *J. Bacteriol.* 167:616–622 (1986)), was used to temporarily complement the Δcrp mutation in the chromosome enabling the identification of the Δcya mutation when introduced via transduction. L broth grown cultures of χ3802, χ3803 and χ4325 were transduced with P22HTint propagated on *S. typhimurium* χ3670, which contains the plasmid pSD10 (Table 1.B.). Selection was made on MacConkey agar+1% maltose+100 μg ampicillin/ml. After 26 h, an ampicillin-resistant, $Mal^+$ colony of each strain was picked and purified on Macconkey agar+1% maltose agar+100 μg ampicillin/ml and designated χ3824 (Ty2), χ3845 (ISP2822) and χ4331 (ISP1820) which all have the genotype Δ[crp-cysG]-10 Δ[zhc-1431::Tn10] $pSD110^+$.

Strains χ3824, χ3845, and χ4331 were grown in L broth+100 μg ampicillin/ml and were each independently transduced with P22HTint propagated on χ3711 to introduce the linked Δcya-12 and zid-62::Tn10 mutations. The transduction mixtures were plated on MacConkey agar+1% maltose+100 μg ampicillin/ml+12.5 μg tetracycline/ml. Ampicillin-resistant ($pSD110^+$), tetracycline-resistant (zid-62::Tn10), $Mal^-$ (Δcya) colonies were picked and purified on MacConkey agar+1% maltose+100 μg ampicillin/ml+ 12.5 μg tetracycline/ml. Purified colonies were picked into L broth, grown to turbidity and the strains checked for complete LPS, Vi antigen and auxotrophy for cysteine and tryptophan. The resulting strains were designated χ3919 (Ty2), χ3920 (ISP2822) and χ4340 (ISP1820) which all have the genotype Δ[crp-cysG]-10 Δ[zhc-1431::Tn10] $pSD110^+$Δcya-12 zid-62::Tn10. Cultures of χ3919, χ3920 and χ4340 were grown in L broth+100 μg ampicillin/ml+ 12.5 μg tetracycline/ml to turbidity, diluted 1:10 into BSG, and 100 μl samples of each culture spread onto fusaric acid-containing media and incubated approximately 36 h at 37° C. Fusaric acid-resistant colonies of each strain were picked and purified onto FA medium. Purified FA-resistant colonies were picked into L broth, grown to turbidity and then checked for loss of Tn10 (tetracycline sensitivity), complete LPS, Vi antigen and auxotrophy for cysteine, arginine and tryptophan. The pSD110 plasmid was usually spontaneously lost from the strains during this process to result in ampicillin sensitivity. The final strains were designated χ3924 (Ty2), χ3925 (ISP2822) and χ4345 (ISP1820) which all have the genotype Δ[crp-cysG]-10 Δ[zhc-1431::Tn10] Δcya-12 Δ[zid-62::Tn10] (Table 1.C.). *S. typhi* Vi antigen synthesis was confirmed by slide agglutination with antisera to Vi (Difco Laboratories, Detroit, Mich.) and by ViII bacteriophage sensitivity by the Luria soft agar overlay technique. Synthesis of flagella is dependent on functional cya and crp genes. However, since flagella are a potentially important antigen, motile derivatives of Δcya Δcrp *S. typhi* strains, due to mutation in the cfs (constitutive flagellar synthesis) gene (Silverman and Simon, *J. Bacteriol.* 120:1196–1203 (1974), were selected in motility agar. Strains χ3940 (ISP2822), χ4073 (Ty2) and χ4346 (ISP1820) were selected as flagella-positive motile derivatives of χ3925, χ3924 and χ4345, respectively.

Fermentation of sugars and growth on various carbon sources of the Δ[crp-cysG]-10 mutant strains were the same as observed for the Δcrp-11 mutant strains. The phenotypes are as expected based on published reports of the requirement for cyclic AMP and the cyclic AMP receptor protein for catabolic activities.

Genetic stability of avirulent mutants. Strains to be orally administered as live vaccines must have complete stability with regard to their avirulence attributes. When 50-fold concentrated cultures and various dilutions (~$10^9$, $10^7$, $10^5$, $10^3$ CFU/plate) of the Δcya Δcrp *S. typhi* strains were plated on minimal agar media (supplemented with required amino acids) containing 0.5% maltose, melibiose, xylose,,glycerol, or rhamnose that should not support their growth, revertants and mutants were not detected. One set of duplicate plates was UV-irradiated (5 joules/meter$^2$/sec) and incubated at 37° C. in the dark. The other set of plates was incubated at 37° C. with illumination. Revertants and mutants were not detected after a 48 h growth period. An investigation was also conducted as to whether tetracycline-resistant revertants/mutants could be recovered at frequencies higher than could be observed for the parental strain. In all cases, such tetracycline-resistant revertants/mutants were not observed.

Example 7

This Example describes the construction of recombinant avirulent *S. typhi* strains expressing foreign antigens for use as oral vaccines to immunize against various infectious diseases.

Bacterial strains. The *E. coli, S. typhimurium* and *S. typhi* strains used are listed in Table 1. The maintenance and storage of these strains are as described in Example 1.

Media. Complex media for routine cultivation, enumeration and identification of bacteria are as described in Example 1.

Transduction and fusaric acid selection for loss of Tn10. The media and methods are as described in Example 1.

Construction of *S. typhi* strains with ΔasdA1 mutation. The wild-type, virulent *S. typhi* Ty2 (type E1) was genetically modified as described below, using classical genetic methods similar to those described in Curtiss and Kelly (1987) and Nakayama, Kelly and Curtiss (1988). The construction of strains χ3927 and χ4323 containing the Δcya-12 Δcrp-11 mutations was described in Example 5. The construction of strain χ4346 containing the Δ[crp-cysG]-10 mutations was described in Example 6. The stable maintenance and high-level expression of cloned genes on recombinant plasmids in avirulent Salmonella strains is dependent upon use of a balanced-lethal host-vector system. For this, a chromosomal mutation of the asd gene encoding aspartate β-semialdehyde dehydrogenase is introduced into a Δcya Δcrp mutant to impose an obligate requirement for diaminopimelic acid (DAP) which is an essential constituent of the rigid layer of the bacterial cell wall and which is not synthesized in animals. The chromosomal Δasd mutation is then complemented by a plasmid cloning vector possessing the wild-type $asd^+$ gene. Loss of the plasmid results in DAPless death and cell lysis. Such balanced-lethal host-vector combinations are stable for several weeks in the immunized animal host and elicit strong immune responses against the cloned gene product as well as against Salmonella.

The construction strategy consists of mobilizing the ΔasdA1 mutation that has been isolated and characterized in *S. typhimurium* LT2-Z (χ3520) into a Δcya Δcrp *S. typhi* strain. This was accomplished by placing the transposon Tn10 (encoding tetracycline resistance) nearby the ΔasdA1 mutation and transducing the linked traits into the *S. typhi* Ty2 Δcya-12 Δcrp-11 strain χ3927, the *S. typhi* ISP1820 Δcya-12 Δcrp-11 strain χ4323 and the *S. typhi* ISP1820 Δcya-12 Δ[crp-cysG]-10 strain χ4346 via P22HTint transduction with selection for tetracycline resistance and screening for a diaminopimelic acid (DAP)-negative phenotype. The zhf-4::Tn10 linked to ΔasdA1 was used for this purpose.

Transduction of the gene deletion with the linked transposon was facilitated by first making a high-titer bacteriophage P22HTint lysate on *S. typhimurium* χ3520 containing the ΔasdA1 and zhf-4::Tn10 mutations. The resulting P22HTint lysate was then used to infect and transduce the genetic traits into the recipient *S. typhi* Ty2 strain χ3927, the ISP1820 strains χ4323 and χ4346 at a multiplicity of infection of 10.

The phage-bacteria infection mixture was incubated for 20 min at 37° C. before 100 μl samples were spread onto Penassay agar (Difco Laboratories, Detroit, Mich.) containing 50 μg DAP/ml and supplemented with 12.5 μg tetracycline/ml. After approximately 26 h incubation at 37° C., transductants were picked and purified on the same medium. A screening of five tetracycline-resistant colonies yields approximately four to five transductants that are also DAP-requiring. The resulting Ty2 derivative was designated χ4296 and has the genotype Δcrp-11 Δ[zhc-1431::Tn10] Δcya-12 Δ[zid-62::Tn10] ΔasdA1 zhf-4::Tn10. The resulting ISP1820 derivatives were designated χ4416 with the genotype Δ[crp-cysG]-10 Δ[zhc-1431:: Tn10] Δ[zid-62::Tn10] ΔasdA1 zhf-4::Tn10 and χ4434 with the genotype Δcrp-11 Δ[zhc-1431::Tn10] Δcya-12 Δ[zid-62::Tn10] ΔasdA1 zhf-4::Tn10. Strains χ4296, χ4416 and χ4434 were grown in L broth+50 μg DAP/ml+12.5 μg tetracycline/ml and was diluted 1:10 into buffered saline with gelatin (BSG), 100 μl was spread onto fusaric acid-containing (FA)+50 μg DAP/ml medium (Maloy and Nunn, 1981) and the plates were incubated approximately 36 h at 37° C. Fusaric acid-resistant colonies were picked into 0.5 ml BSG and purified onto FA+50 μg DAP/ml media. Purified fusaric acid-resistant colonies were picked into L broth+50 μg DAP/ml and grown at 37° C. to turbidity and checked for loss of Tn10 (tetracycline sensitivity), presence of complete LPS and Vi antigen and auxotrophy for cysteine, tryptophan, methionine, threonine and DAP on minimal media. The new strains were designated χ4297 (Ty2), which has the genotype Δcrp-11 Δ[zhc-1431::Tn10] Δcya-12 Δ[zid-62::Tn10] ΔasdA1 Δ[zhf-4::Tn10]; χ4417 (ISP1820), which has the genotype Δ[crp-cysG]-10 Δ[zhc-1431::Tn10] Δcya-12 Δ[zid-62::Tn10] ΔasdA1 Δ[zhf-4::Tn10]; and χ4435 (ISP1820), which has the genotype Δcrp-11 Δ[zhc-1431::Tn10] Δcya-12 Δ[zid-62::Tn10] ΔasdA1 Δ[zhf-4::Tn10].

$Asd^-$ derivatives of the wild-type parent strains were constructed for the purpose of comparing the production of a recombinant antigen expressed by a $Crp^+$ $Cya^+$ background versus a $Crp^-$ $Cdt^-$ $Cya^-$ background. The Ty2 ΔasdA1 strain was constructed by cotransducing *S. typhi* Ty2 strain χ3769 and the *S. typhi* ISP1820 strain Δ3744 with P22HTint(χ3520), selecting tetracycline resistance and screening for a diaminopimelic acid-negative phenotype. The resulting Ty2 derivative was designated χ4456 and the ISP1820 derivative was designated χ4454 and both have the genotype ΔasdA1 zhf-4::Tn10. Strains χ4456 and χ4454 were grown in L broth+50 μg DAP/ml+12.5 μg tetracycline/ml and was diluted 1:10 into buffered saline with gelatin (BSG), a 100 μl sample was spread onto fusaric acid containing+50 μg DAP/ml medium (Maloy and Nunn, 1981), and the plates were incubated approximately 35 h at 37° C. Fusaric acid-resistant colonies were picked into L broth+50 μg DAP/m and grown at 37° C. to turbidity and checked for loss of Tn10 (tetracycline sensitivity), presence of complete LPS and Vi antigen, and auxotrophy for cysteine, tryptophan, methionine, threonine and DAP on minimal media. The new strains were designated χ4457 (Ty2) and χ4455 and have the genotype ΔasdA1 Δ[zhf-4::Tn10].

Expression of a *Mycobacterium leprae* antigen in avirulent recombinant *S. typhi*. λgt11::*Mycobacterium leprae* clone L14 (also designated clone 7.8) was identified by immunological screening of a λgt11::*M. leprae* library with pooled sera from 21 lepromatous (LL) leprosy patients (Sathish, Esser, Thole and Clark-Curtiss, *Infect. Immun.* 58: 1327–1336 (1990)). Clone L14 specifies two proteins of approximately 158 and 153 kDa, both of which react very strongly with antibodies in the pooled LL patients' sera (Sathish et al., 1990). These proteins also react with antibodies in 14 out of the 21 LL patients' sera when the sera were tested individually (Clark-Curtiss, Thole, Sathish, Bosecker, Sela, de Carvalho and Esser, *Res. in Microbiology*, in press).

Figure 2:
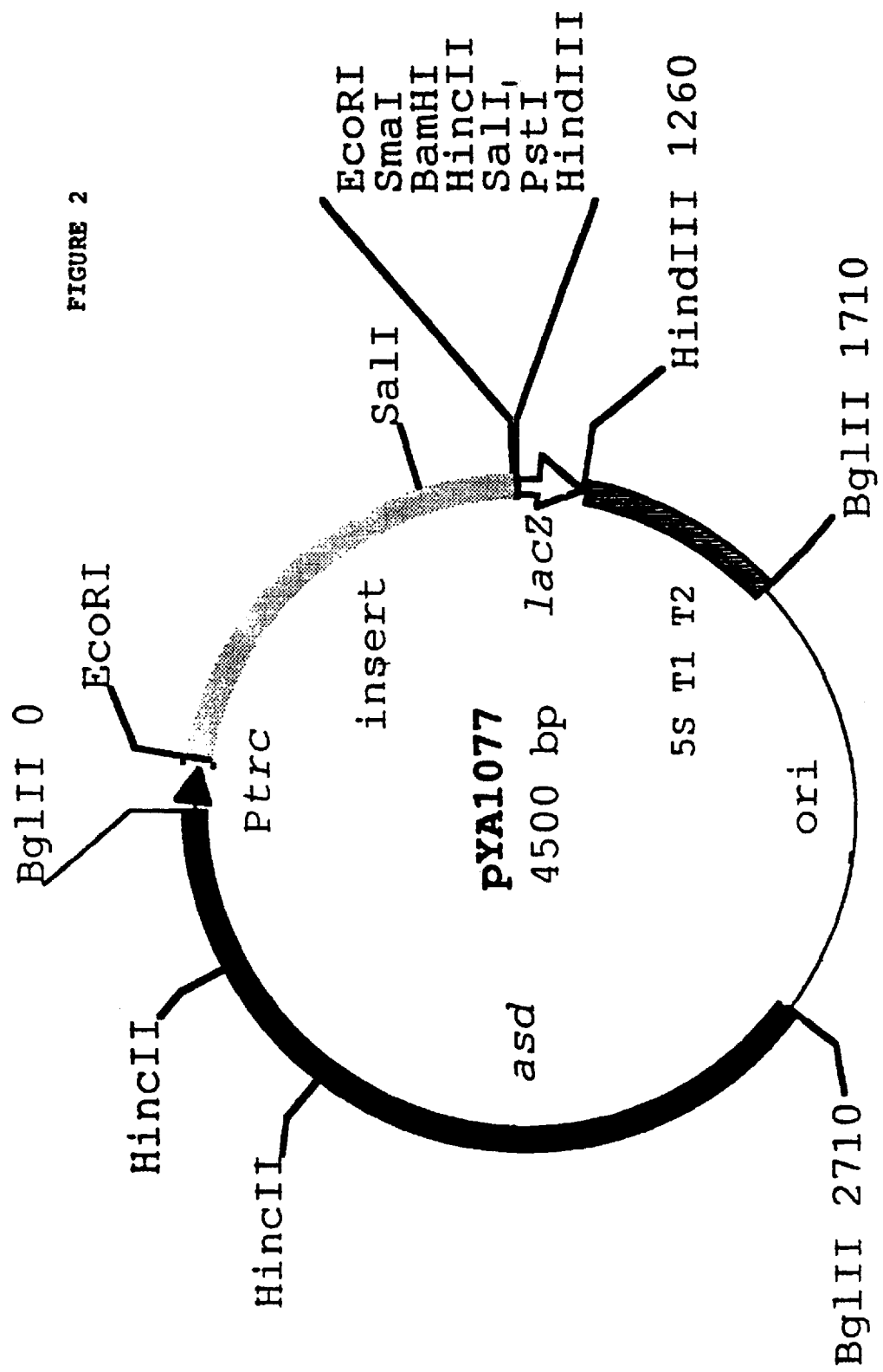
FIG. 2 is a partial restriction map of pYA1077. The 1.0 kb M. leprae insert DNA fragment from $\lambda$gt11 clone L14 was subcloned into the EcoRI site of pYA292. There is a single asymmetrical SalI site within the M. leprae insert DNA. There are no sites within the M. leprae insert DNA for the following restriction endonucleases: BamHI, HindIII, PstI, and XbaI.

The 1.0 kb *M. leprae* insert DNA fragment was removed from λgt11 clone L14 by digestion of the recombinant phage DNA with EcoRI, followed by separation of the digestion fragments by agarose gel electro-phoresis. The *M. leprae* fragment was purified from the gel and cloned into the EcoRI site of the Asd$^+$ vector pYA292 (Galan, Nakayama and Curtiss, *Gene* (1990), 94:29). Two kinds of recombinant plasmids were generated: pYA1077, in which the *M. leprae* insert DNA was cloned into pYA292 in the same orientation relative to the trc promoter as it was in λgt11 relative to the lacZ promoter, and pYA1078, in which the *M. leprae* fragment was cloned in the opposite orientation relative to the trc promoter. A partial restriction map of pYA1077 is presented in FIG. 2. Both recombinant plasmids were transformed into *Escherichia coli* K-12 strain χ6060 and *S. typhimurium* strain χ3730 and the proteins specified by the transformants were analyzed by Western blotting. Clone pYA1077 specifies a single fusion protein of approximately 30 kDa, which reacts strongly with antibodies in the pooled LL patients' sera. Clone pYA1078 does not specify any protein that reacts with the patients' sera.

Figure 3:
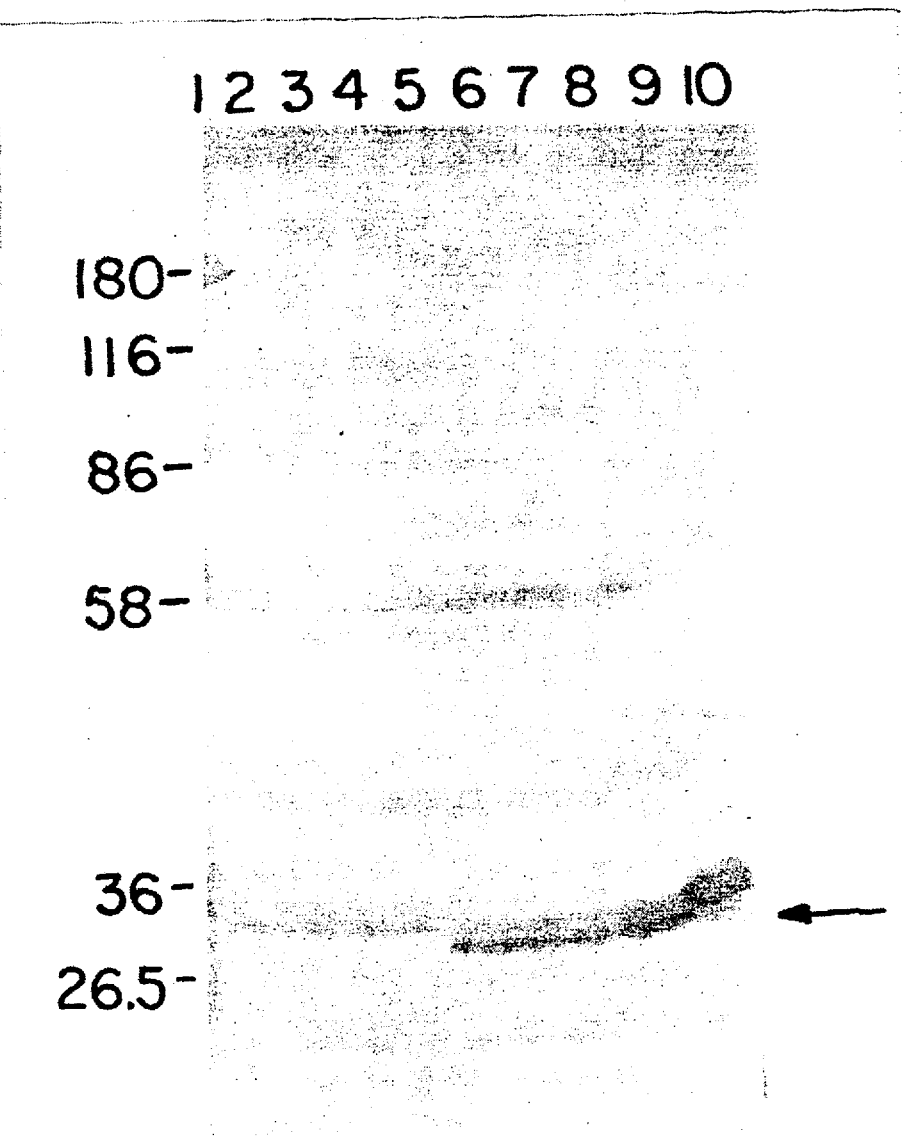
FIG. 3 is a half-tone reproduction showing a Western blot of proteins produced by S. typhi, S. typhimurium, and E. coli strains harboring pYA1077 and pYA1078. The proteins on the nitrocellulose filters were reacted with pooled sera from 21 lepromatous leprosy patients. Lane 1, molecular size markers (sizes are indicated to the left of the blot); Lane 2, proteins specified by S. typhi $\chi4297$ with pYA292; Lanes 3 to 5, proteins specified by three independent S. typhi $\chi4297$ isolates each containing pYA1078; Lanes 6 to 8, proteins specified by three independent isolates of S. typhi $\chi4297$ isolates each containing pYA1077; Lane 9, proteins specified by S. typhimurium $\chi4072$ with pYA1077; Lane 10, proteins specified by E. coli $\chi6060$ with pYA1075 (a pUC8-2 derivative containing the 1.0 kb M. leprae DNA insert from $\lambda$gt11 clone L14 in the same orientation relative to the lacZ promoter as it is in pYA1077). Note: the immunologically reactive protein specified by pYA1075 is slightly larger than that specified by pYA1077 because it is a fusion protein with the alpha region of $\beta$-galactosidase.

Bacteriophage P22HTint lysates were prepared on *S. typhimurium* χ3730+pYA1077 and χ3730+pYA1078; these lysates were used to transduce *S. typhi* χ4297, χ4417, χ4435, χ4455, and χ4457. Western blot analysis of the proteins produced by three randomly chosen transductants of χ4297 with pYA1077 showed that each transductant specified a protein of 30 kDa that reacted with the pooled LL patients' sera whereas three independent χ4297 transductants harboring pYA1078 did not specify an immunologically reactive protein (FIG. 3).

Figure 4:
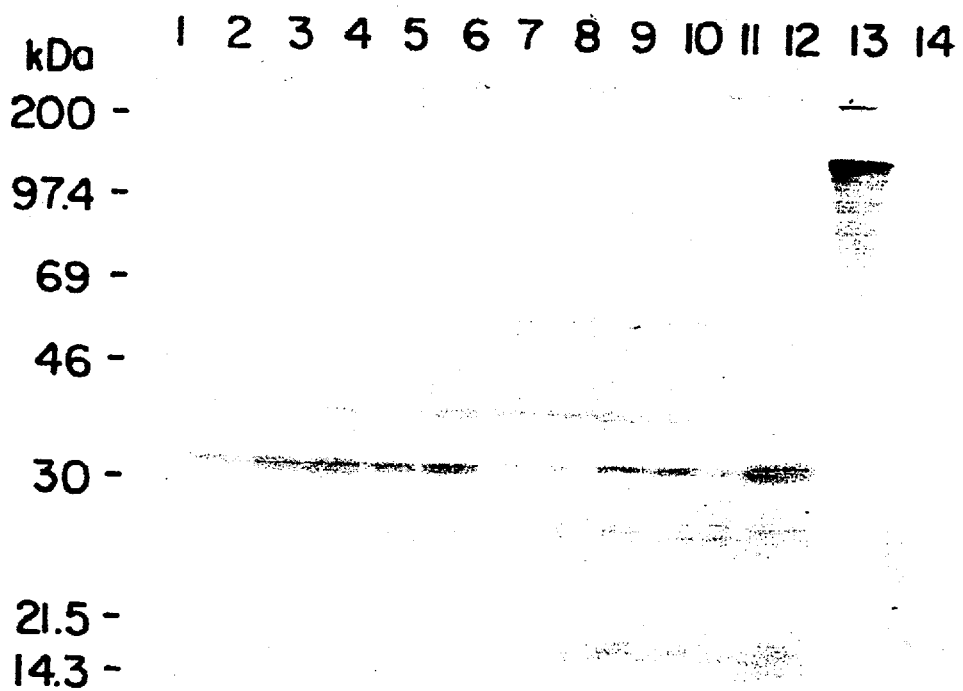
FIG. 4 is a half-tone reproduction showing a Western blot of proteins produced by $\lambda$gt11::M. leprae clone L14 and S. typhi, S. typhimurium and E. coli strains harboring pYA292, pYA1077 and pYA1078.
Figure 5:
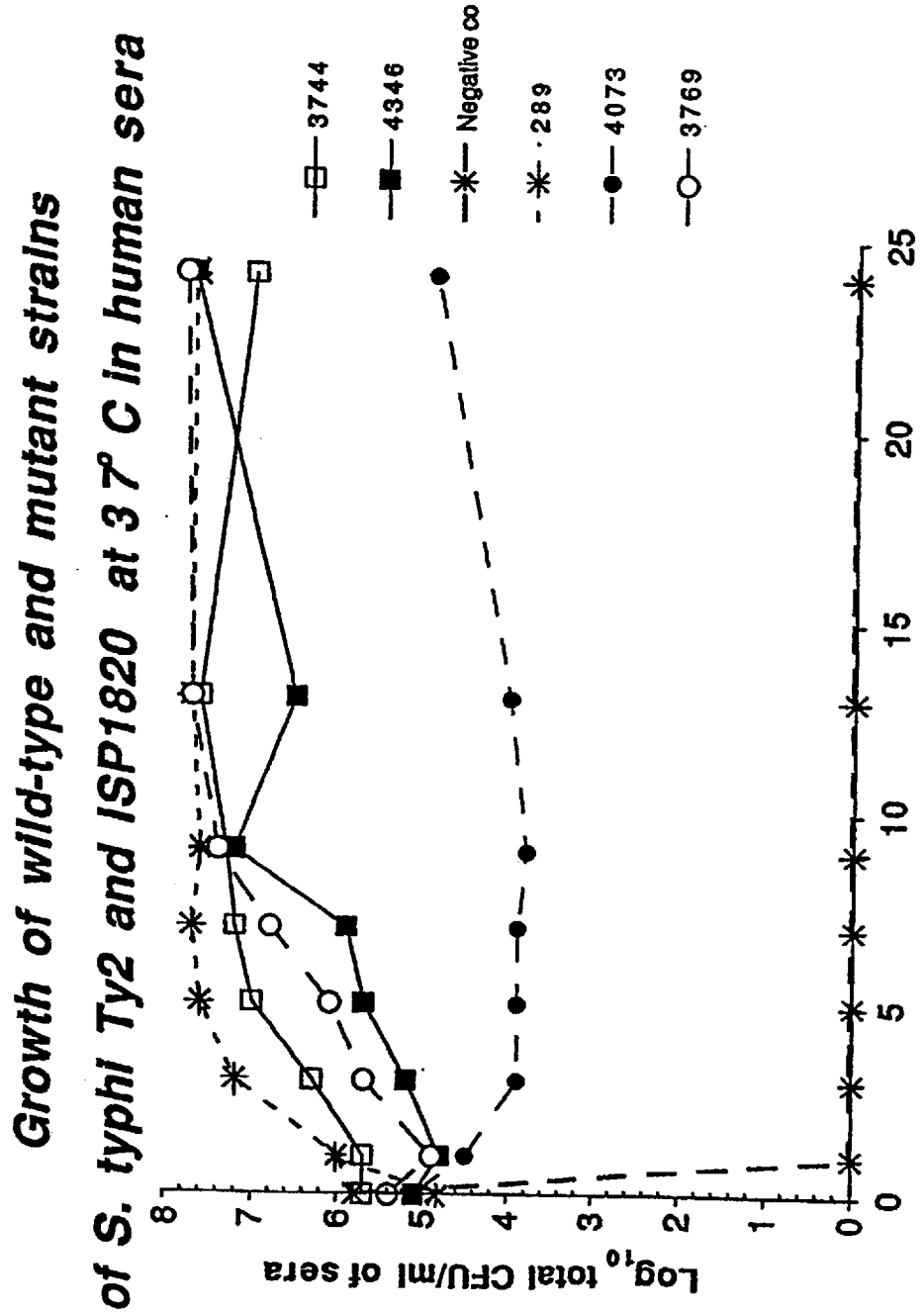
FIG. 5 is a graph showing the growth of wild-type and mutant strains of S. typhi Ty2 and ISP1820 at 37° C. in human sera.

In addition, expression of immunologically reactive proteins from pYA1077 was also shown in χ4417, χ4435, χ4455, and χ4457. FIG. 4 shows a Western blot of proteins produced by λgt11:*M. leprae* clone L14 and *S. typhi, S. typhimurium* and *E. coli* strains harboring pYA292, pYA1077 and pYA1078. The proteins on the nitrocellulose filter were reacted with pooled sera from 21 lepromatous leprosy patients. Positive antigen-antibody were detected by the technique described by Sathish, Esser, Thole and Clark-Curtiss (1990) 58:1327. More specifically, the secondary antibody was alkaline phosphatase-conjugated anti-human polyspecific antibodies and the chromogenic substrates were nitro blue tetrazolium and 5-bromo-4-chloro-3-indolyl phosphate, p-toluidine salt. The lanes in the figures are as follows: (lane 1) molecular size markers; (lane 2) *S. typhi* χ4297 with pYA1077; (lane 3) *S. typhi* χ4417 with pYA1077; (lane 4), *S. typhi* χ4435 with pYA1077; (lane 5) *S. typhi* χ4455 with pYA1077; (lane 6) *S. typhi* χ4457 with pYA1077; (lane 7) *S. typhi* χ4297 with pYA292; (lane 8) *S. typhi* χ4435 with pYA292; (lane 9) *S. typhi* χ4455 with pYA292; (lane 10) *S. typhi* χ4457 with pYA292; (lane 11) *S. typhi* χ4417 with pYA292; (lane 12) *E. coli* χ6097 with pYA1077; (lane 13) proteins from λgt11*::M. leprae* clone L14; (lane 14) *S. typhimurium* χ4072 with pYA1078. The immunologically reactive proteins specified by λgt11*::M. leprae* clone L14 are larger in size because they are fusion proteins with β-galactosidase.

The *S. typhi* strains χ4297, χ4417 and χ4435 with the pYA1077 recombinant vector are candidates to immunize humans to protect against typhoid fever and leprosy. Efficacy of such vaccines will be dependent upon identifying one to several *M. leprae* antigens that would elicit protective immune responses and having them specified by cloned genes in an $Asd^+$ vector in the *S. typhi* Δcya Δcrp Δcdt Δasd strains which could then be used in human immunization trials.

Example 8

This example provides a procedure for testing the safety, immunogenicity, and efficacy of live oral vaccines comprised of Δcya Δcrp mutants of *S. typhi*. The strains tested are Δcya Δcrp derivatives of Ty2, ISP1820 and ISP2822.

The Individuals Studied. The individuals studied are volunteers who are healthy adult humans aged 18–39 years. The prospective volunteers are screened before the study. The screening procedure includes:

1. medical history
2. physical examination
3. electrocardiogram
4. urinalysis
5. complete blood count
6. blood chemistries (BUN, creatinine, fasting blood glucose
7. Serum $Na^+$, $Cl^-$, $K^+$, $HCO_3^-$
8. VDRL
9. Hepatitis B surface antigen
10. HIV antibody by ELISA
11. Pregnancy test (females)
12. Liver function tests (SPGT)
13. Psychological examination and interviews.

The Volunteers to participate in the study are selected on the basis of general good health and have:

1. no clinically significant history of gall bladder disease, immunodeficiency, cardiovascular disease, respiratory disease, endocrine disorder, liver disease including a history of hepatitis, renal and bladder disease, enlarged prostate, glaucoma, gastrointestinal disease, disorder of reticuloendothelial system, neurologic illness, psychiatric disorder requiring hospitalization, drug or alcohol abuse;
2. normal and regular bowel habits falling within the limits defined for a normal population: at least 3 stools per week and less than 3 stools per day without frequent use of laxatives or antidiarrheal agents;
3. absence of allergy to amoxicillin or ciprofloxacin;
4. no history of any antibiotic therapy during the 7 days before vaccination;
5. a negative pregnancy test (females);
6. a negative HIV antibody test.

The Volunteers are admitted to an Isolation Ward, and informed, witnessed, written consent is obtained.

Study design. Groups of 22 volunteers are studied. Baseline blood and intestinal fluid specimens are collected. After a two-day period of acclimatization on the ward, the fasting volunteers are randomly allowed to ingest with bicarbonate buffer a single oral dose containing $5\times10^5$ of either the Δcya Δcrp derivative of Ty2, ISP1820 or ISP2822. The volunteers are observed for the next 15 days for adverse reactions (fever, malaise, chills, vomiting, diarrhea)(the usual incubation period of typhoid fever is 8–12 days). Serial blood and stool cultures are obtained. In addition, any volunteer who has a temperature elevation to 100.8° F. has blood samples drawn at the time the observation is made; if the temperature remains elevated at this level for 12 hours, therapy is initiated with oral amoxicillin (1.0 gram every 6h) and oral ciprofloxacin (750 mg every 12h for 10 days). Duodenal fluid cultures are also obtained during the period of observation on days 7, 10, and 13.

Animal tests. The $LD_{50}$s for the parent strains and attenuated derivatives in mice by intraperitoneal inoculation with hog gastric mucin as adjuvant are also determined.

Preparation of the vaccine inocula. Stock cultures of the S. typhi candidate vaccine strains are stored as a cell suspension in trypticase soy broth (TSB), supplemented with 15% glycerol, at −70° C. until needed. To make an inoculum of each strain, the suspension is thawed and plated onto sheep red blood cell agar (5% srbc in TSA), two days before challenge. After incubation at 37° C. overnight, about 20–30 typical colonies are picked and suspended in saline. This suspension is inoculated onto trypticase soy agar plates, appropriately supplemented, and the plates incubated overnight at 37° C. In preparation for orally vaccinating the volunteers, growth on these plates is harvested with approximately 3 ml sterile normal saline per plate. The resulting suspension is standardized turbidimetrically. Dilutions are made in saline to approximate the concentration of Salmonella required. The vaccine inoculum is transported to the isolation ward on ice. Microscopic examination and slide agglutination with *S. typhi* O and H antisera are performed before use. Replica spread plate quantitative cultures are made of the inocula before and after vaccination to confirm viability and inoculum size.

Inoculation of Volunteers. The vaccine is administered by the oral route with $NaHCO_3$. Volunteers are NPO for 90 minutes before vaccination. Two grams of $NaHCO_3$ are dissolved in 5 ounces of distilled water. Volunteers drink 4 ounces of the bicarbonate water; one minute later the volunteers ingest the vaccine suspended in the remaining 1 ounce of bicarbonate water. Volunteers take no food or water for 90 minutes after inoculation.

Procedures for Specimen Collection.

Stool specimens. A record is kept of the number, consistency, and description of all stools passed by volunteers. A specimen of every stool (or rectal swab if stool is not passed) is collected for culture. The volume of the specimen is measured. Stools are graded on a five point system:

grade 1-firm stool (normal)

grade 2-soft stool (normal)

grade 3-thick liquid (abnormal)

grade 4-opaque watery (abnormal)

grade 5-rice water (abnormal).

Phlebotomy. Serum for antibody determinations is obtained before and 8, 21, 28, 60, and 180 days after vaccination. Heparinized blood for lymphocyte separations for antibody-secreting cell assays is collected on days 0, 4, 7, and 10. Mononuclear cells collected on days 0, 28, 60, and 180 days are used to assess lymphocyte proliferative responses to Salmonella and control antigens. Lastly mononuclear cells from days 0, 28, 60, and 180 are also used in the antibody-dependent cytotoxicity assay against *S. typhi* and control organisms. Blood (5 ml) is obtained for culture on days 3, 4, 7, 8, 10, 12, and 15 during the post-vaccination observation period to detect vaccine organisms. An additional specimen of serum and mononuclear cells are obtained 180 days after primary vaccination.

Jejunal fluid aspiration. Before oral vaccination and immediately before discharge (day 15), volunteers swallow polyvinyl chloride intestinal tubes to a distance of 130 cm from the mouth to collect intestinal fluid for measurement of local SIgA antibody. Ten mg of metoclopramide is given orally after ingestion of the tube to accelerate its passage from the stomach through the pylorus into the small intestine. Placement of the tubes in the jejunum is verified by distance (130 cm), color (yellow-green), and pH (6) of aspirated fluid. Approximately 100 ml of jejunal fluid is removed at each intubation.

Gelatin String Capsules. In order to determine rates of intestinal colonization with each vaccine strain, gelatin string capsules (Entero-Test) are ingested by volunteers three times during the period of hospitalization.

The volunteer is NPO from 6 A.M. A swallow of water is used to moisten the mouth and throat. The capsule, with a portion of the string pulled out, is swallowed with water while holding the loop of the nylon string. The line is secured to the face, and left in place for 4 hours. The volunteers are allowed to drink water ad lib, but are not allowed other food or beverages. After 4 hours, the line is withdraw, the distal section saturated with bile stained mucus is cut and placed in a sterile petri dish, which is labeled for identification. The strings are then cultured for microorganisms, using the same method as with the stool specimens.

Tonsillar Cultures. In order to detect possible invasion of tonsillar lymph tissue after vaccination, serial tonsillar cultures are obtained on days 3, 4, 7, 8, 10, 12, and 15.

Bacteriological Analysis. Stools, rectal swabs, and the distal 15 cm of bile-stained duodenal string from the ingested gelatin capsule is inoculated into selenite F enrichment broth. Tonsillar swabs are inoculated into GN broth. After overnight incubation at 37° C., subcultures are made onto Salmonella-Shigella agar and XLD agar, both appropriately supplemented for the auxotrophy of the vaccine strain. Suspicious colonies are transferred to supplemented triple sugar iron slants and confirmation made by agglutination with *S. typhi* Vi, O, and H antisera. These isolates are saved at −70° C. in glycerol for further analysis (e.g., for the presence of plasmids or for Southern blotting with specific gene probes for cloned genes).

Blood cultures (5 ml) are inoculated into 50 ml of supplemented brain heart infusion broth.

Immunological Analysis. Sera and jejunal fluid specimens are tested for IgA, IgM, and IgG antibodies to *S. typhi* O, H, and Vi antigens measured by ELISA, using the procedures described by Levine et al. (1987), J. Clin. Invest. 79:888–902. H antibody is also measured by Widal tube agglutination using *S. virginia* as antigen (*S. virginia* shares an identical flagellar antigen with *S. typhi*).

Peripheral blood mononuclear cells are collected and separated for studies of specific responses to Salmonella antigens. These include the following.

1. Antibody-secreting cells: trafficking lymphocytes which secrete IgG, IgA or IgM antibody against *S. typhi* O, Vi or H antigens are measured by the method of Kantele et al.

2. Replicating lymphocytes: peripheral blood mononuclear cells are mixed with heat-phenol-inactivated *S. typhi, S. typhimurium, S. thompson*, and *E. coli* to detect antigen-driven lymphocyte replication, as described in Levine et al., supra.

3. ADCC: plasma-mediated mononuclear cell inhibition of *S. typhi* is measured in an antibody dependent cellular cytotoxicity assay as described in Levine et al., supra.

Excretion of the Vaccine Strain. It is expected that excretion of the vaccine strain would cease within 1 week after a dose of vaccine. If excretion continues for 7 or more days, the volunteer who continues to excrete is given a dose of ciprofloxacin (750 mg every 12 hours). Negative cultures for $\geqq 2$ consecutive days are required for discharge.

Example 9

This example demonstrates the safety and immunogenicity of a Δcya Δcrp *S. typhi* strain, χ3927, which was prepared from the wild-type parent strain, Ty2. The $LD_{50}$ in mice of this strain is $1.8 \times 10^4$ (using an intraperitoneal injection with hog gastric mucin).

The procedure followed was essentially that described in Example. 8, supra. Two cohorts of volunteers were used for studies in which different doses of vaccine were given. In the first study, 17 volunteers were randomized in a double-blind fashion; 6 volunteers received $5 \times 10^5$ cfu of χ3927, the remainder received the same dose of other S. typhi strains. In the second study, 19 volunteers were randomized in a double-blind fashion; 6 volunteers received $5 \times 10^4$ cfu of χ3927, the remainder received the same dose of other S. typhi strains. Volunteers were closely monitored on an Isolation Ward for 15 days (first study) or 24 days (second study). Vital signs were measured every six hours during the period of observation. All stools from each volunteer were collected in plastic containers, examined, graded on a five-point scale, and the volume measured if the stool was loose. Volunteers were interviewed daily by a physician and asked about symptoms. Fever was defined as oral temperature $\geq 38.2°$ C.; diarrhea was defined as two or more loose stools within 48 hours totalling at least 200 ml in volume or a single loose stool $\geq 300$ ml in volume. Antibiotic therapy was given to volunteers who developed fever or positive blood cultures.

In order to prepare the vaccine, stock cultures of χ3927 which had been maintained on trypticase soy broth with 15% glycerol at $-70°$ C. were thawed and grown on supplemented aro agar. After incubation at 37° C., 20–30 typical colonies of the vaccine strain were picked from aro agar, suspended in saline, and inoculated again onto aro agar. After overnight incubation at 37° C., the bacteria were harvested with 3 ml of sterile phosphate buffered saline (PBS) and the concentration of bacteria was standardized turbidimetrically. Dilutions of the suspensions were made in PBS to achieve the desired concentration of viable organisms per milliliter. The identity of the inoculum was confirmed by microscopic examination and by side agglutination with S. typhi O, H, and Vi antisera. Replica spread plate quantitative cultures were made of the inocula before and after vaccination to confirm viability and the inoculum size.

The vaccine strains were administered by the oral route with sodium bicarbonate. Sodium bicarbonate (2 gm) was dissolved in 150 ml of distilled water and volunteers drank 120 ml to neutralize gastric acid. One minute later, volunteers drank the vaccine suspended in the remaining 30 ml of bicarbonate solution. Volunteers had nothing to eat or drink for 90 minutes before and after vaccination.

Every stool passed by volunteers (and rectal swabs if no stool was passed) was cultured daily for the vaccine strain. Stool was inoculated into Gram Negative broth (BBL, Cockeysville, Md.) supplemented with 0.1% PABA and 0.1% PHB and directly onto S—S agar with supplements. After incubation overnight at 37° C., subcultures were made onto supplemented S-S agar. To quantitate the shedding of vaccine strains, 1 g of stool was serially diluted 10-fold in saline and each dilution was plated onto S—S agar supplemented as above. Suspicious colonies were transferred to triple sugar iron agar slants and the identity confirmed by agglutination with S. typhi O, H, and Vi antisera.

On days 7, 10, and 13 after vaccination, fasting volunteers swallowed gelatin capsules containing string devices to collect samples of bile-stained duodenal fluid. After 4 hours, the strings were removed and the color and pH of the distal 15 cm were recorded. Duodenal fluid was squeezed from the end of the string and cultured as above.

Blood for culture of the vaccine organisms was systematically collected on days 4, 5, 7, 8, 10, 12, and 15 after vaccination and again if fever occurred. Five ml of blood was inoculated into 50 ml of supplemented aro broth.

In addition, tonsillar cultures were obtained on days 1, 2, 4, 5, 7, 8, 10, 12 and 15 to detect the vaccine strain. Swabs applied to the tonsils were inoculated into Gram Negative broth with supplements for 24 hours and then onto supplemented salmonella-shigella agar.

In order to determine the immunological response, the following procedures were followed. Serum samples were obtained before and on days 7, 21, 28, and 60 after vaccination. Jejunal fluids were collected before and on day 14 after vaccination, as described in Example 8. The total IgA content of the fluids were measured by ELISA and each specimen was standardized to contain 20 mg of IgA per 100. Antibodies to S. typhi lipopolysaccharide (LPS), H, and Vi antigens were measured in serum and jejunal fluids.

IgG antibody to LPS O antigen was detected by ELISA. A rise in net optical density $\geq 0.20$ between pre- and post-vaccination sera tested at a 1:100 dilution was considered a significant rise. The positive control serum used with each microtiter plate contained a high level of LPS O antibody and represented a pool of sera from 12 healthy Chileans who had strong IgG LPS O antibody responses after immunization with Ty21a vaccine. IgA antibody to LPS O antigen was measured using two-fold dilutions of serum, starting with a 1:25 dilution. An IgA titer was considered significant if a 4-fold rise occurred between pre- and post-vaccination procedures.

Intestinal secretory IgA antibody to S. typhi LPS O antigen was also measured by ELISA. Four-fold rises were considered significant.

In order to measure H antibody, H-d flagellar antigen was prepared from S. typhi strain 541 Ty. Serum and jejunal fluid for H-d antibody was measured by ELISA. A 4-fold rise in titer was considered significant.

The Widal tube agglutination test for H antibody was performed using Salmonella virgina which shares the flagellar antigen d with S. typhi, but no other antigens.

Vi antibody was measured in serum and jejunal fluid by ELISA; a 4-fold rise was considered significant.

Gut-derived, trafficking antibody secreting cells (ASC) that secrete IgG, IgA, or IgM antibody against S. typhi O, H, or Vi antigens were measured by a modification of the method of Forrest et al. ((1988), Lancet 1:81) using both ELISA and ELISPOT assays. Heparinized blood was drawn before and on days 7 and 10 after vaccination. Briefly, peripheral blood lymphocytes separated by a Ficoll gradient (Organon Teknika, Durham, N.C.) were added to antigen-coated plates. In the ELISA, binding of antibody secreted by lymphocytes was measured by the change in optical density produced by the reaction of the substrate with bound anti-IgA conjugate. Significant responses to LPS, H, and Vi antigens were determined using the differences in O.D. pllus 3 S.D. generated from pre-immunization and day 4 cells taken from volunteers participating in these studies. In the ELISPOT assay, specific IgA secreted by individual lymphocytes was detected by adding an agarose overlay to each well and counting colored spots produced by reaction of the substrate with bound anti-human IgA conjugate. Detection of $\geq 4$ spots per well after vaccination was defined as a positive response; this number is based on the mean number of spots counted before vaccination plus 2 S.D.

The results obtained were the following.

The clinical signs and symptoms of volunteers after vaccination were evaluated in a double-blind fashion. One of 12 volunteers who received strain χ3927 had fever. This volunteer developed fever with a maximum temperature of 40.1° C. on day 22 after vaccination. This volunteer had severe abdominal cramps, malaise, anorexia, headache, and vomiting on days 4–13, but his fever did not begin until day 22. His symptoms then included dizziness, muscle and body aches, constipation, insomnia, and cough productive of brown sputum. Another volunteer in this group had malaise, cramps, headache, and nausea during the inpatient surveillance period.

The bacteriology studies showed that one of six volunteers who received $5\times10^4$ and one of six volunteers who received $5\times10^5$ cfu of χ3927 had positive blood cultures. These occurred on days 15 and days 8 and 12, respectively. Neither of these volunteers had any symptoms. One of the 12 volunteers who received χ3927 had one colony of vaccine organisms detected in the stool on day 1. None of these volunteers had positive tonsillar or duodenal string cultures. The χ3927 isolates recovered from the blood and the stool of volunteers retained all expected phenotypes associated with the presence of Δcya Δcrp mutations.

The immunological studies showed that six (50%) of the 12 vaccines who received χ3927 developed IgG anti-S. typhi LPS responses. No antibody to H antigen or Vi were detected in any of the twelve volunteers. Only one of the twelve volunteers developed secretory IgA against LPS in the jejunal fluid. Secretory IgA antibody responses to H antigen occurred in only one volunteer and no volunteer had secretory anti-Vi antibody after vaccination. Five of 12 volunteers developed circulating cells secreting IgA against LPS detected by ELISA or ELISASPOT assay.

The degree of attenuation conferred by deletions in the cyclic AMP regulatory pathway cannot be strictly measured without simultaneous challenge of volunteers with mutant and parent strains. However, based on historical experience with volunteers given similar doses of wild type strains, it is likely that the deletions confer attenuation to S. typhi. When wild-type S. typhi strain Ty2 was fed to six volunteers at a dose of $1\times10^7$ without bicarbonate, 83% developed typhoid fever (defined as temperature 103° F. for >36 hours) or infection (defined as low grade fever, significant serologic response, positive blood culture, or excretion of S. typhi for >5 days. In contrast, among the 12 volunteers reported herein who received the χ3927 vaccine derived from Ty2 at a dose of $10^4$ or $10^5$ cfu with bicarbonate (equivalent to a much higher dose without bicarbonate), fever occurred in only one volunteer and positive blood cultures in only two volunteers. Moreover, volunteers who had febrile illnesses did not have vaccine bacteria detected in their blood, despite additional blood cultures collected at the time of fever. It is likely that fever occurred in response to the release of cytokines stimulated by the enteric infection with the vaccine.

Example 10

This example describes the construction and characterization of Δcrp-10 Δcya-12 S. typhi constructs which contain a Δcdt mutation. We have introduced Δcya Δcrp mutations into S. typhi Ty2 (type E1) and S. typhi ISP1820 (a Chilean epidemic type 46 isolate). The former strain with Δcya-12 and Δcrp-11 mutations has already been evaluated in human volunteers, described in Example 9. One of six volunteers who received $5\times10^4$ cfu and one of six volunteers who received $5\times10^5$ cfu of the Δcrp-11 Δcry-12 S. typhi strain, χ3927, had positive blood cultures. These occurred on day 15 and days 8 and 12, respectively. However, neither of these volunteers had any symptoms. Furthermore, not all immunized individuals developed high-titer antibody responses to S. typhi antigens. Additional attenuating mutations which would permit higher oral doses for induction of protective immunity in the majority of those immunized, are desirable. We have identified an additional gene defect that has been introduced into Δcya Δcrp S. typhi strains that results in decreased virulence and should thus permit higher dosages. The defect is a deletion in a gene termed cdt for colonization of deep tissues. Strains with a Δcdt mutation, in addition to Δcya and Δcrp mutations are also less able to survive in human serum than are strains with only Δcya Δcrp mutations. They should therefore be cleared more readily and would be less likely to induce vaccinemia.

Strain construction The wild-type, virulent S. typhi Ty2 (Type E1) and ISP1820 (Type 46) strains have been genetically modified using classical genetics by similar methods described in Curtiss and Kelly ((1987), Infect. Immun. 55:3035–3043), and described in Example 1. Salmonella typhimurium deletion mutants lacking adenylate cyclase and cyclic AMP receptor protein are avirulent and immunogenic. Infect. Immun. 55:3035–3043.(1). The strategy consists of facilitating transduction of deletions of crp-cdt (designated Δcrp-10) and cya genes that have been isolated and characterized in S. typhimurium SL1344 by placing a transposon Tn10 (encoding tetracycline resistance) nearby the cya or crp deletion. We have therefore used zhc-1431::Tn10 linked to Δcrp-10 and zid-62::Tn10 linked to Δcya-2, respectively, and cotransduced with P22HTint the linked traits into the highly virulent S. typhi Ty2 and ISP1820 strains with selection for tetracycline resistance and screening for a maltose-negative phenotype.

Transduction of the gene deletion with the linked transposon was facilitated by first making a high-titer bacteriophage P22HTint lysate on an S. typhimurium strain χ3712 containing the Δcrp-10 zhc-1431::Tn10 mutations and another lysate on an S. typhimurium strain χ3711 containing the Δcya-12 zid-62::Tn10 mutations. The resulting P22HTint lysates were then used to infect and transduce the genetic traits into the recipient S. typhi Ty2 (χ3769) and ISP1820 (χ3744) strains at a multiplicity of infection of 10.

P22HTint propagated on S. typhimurium χ3712 (Δcrp-10 zhc-1431::Tn10) was used to transduce the virulent S. typhi Ty2 and ISP1820 strains to Mal⁻ Tet$^r$. The phage-bacteria infection mixture was incubated for 20 min at 37° C. before 100 μl samples were spread onto MacConkey agar (Difco Laboratories, Detroit, Mich.) containing 1% maltose (final concentration) supplemented with 12.5 μg tetracycline/ml. After approximately 26–36 h incubation at 37° C., transductants were picked and purified onto the same media. The resulting Ty2 derivative was designated χ3792 and the ISP1820 derivative was designated χ4324. Both have the genotype Δcrp-10 zhc-1431::Tn10. Strains χ3792 and χ4324 were grown in Luria broth$^1$+12.5 μg tetracycline/ml and each were diluted 1:10 into buffered saline with gelatin (BSG). Samples of 100 μl of each strain were spread onto fusaric acid-containing (FA) media (Maloy and Nunn (1981), J. Bacteriol. 145:1110–1112) and the plates incubated approximately 36 h at 37° C. Fusaric acid-resistant colonies of each strain were picked into 0.5 ml BSG and purified by streaking onto FA media. Purified fusaric acid-resistant colonies were picked into Luria broth and grown at 37° C. to turbidity and checked for loss of Tn10 (tetracycline sensitivity), complete LPS, Vi antigen and auxotrophy for arginine, cysteine and tryptophan. The new strains were designated χ3803 (Ty2) and χ4325 (ISP1820) which have the genotype Δcrp-10 Δ[zhc-1431::Tn10].

[1]Luria broth contains 10 g of NaCl per liter whereas Lennox broth contains 5 g of NaCl per liter. It has been shown that Salmonella cells grown in high osmolarity media display an increased ability to invade tissue culture cells (Galan and Curtiss, Infect. Immun. (1990) 58:1879–1885; expression of Salmonella genes required for invasion is regulated by changes in DNA supercoiling). Therefore, the increased NaCl level in Luria broth ensures optimal effectiveness of the vaccine strain.

Since the phenotype of Cya$^-$ and Crp$^-$/Cdt$^-$ mutants are the same (Mal$^-$, Stl$^-$, Mtl$^-$, etc.), the plasmid, pSD110, carrying the cloned wild-type crp$^+$ gene with its promoter (Schroeder and Dobrogosz (1986), J. Bacteriol. 167:616–622.) was used to temporarily complement the Δcrp mutation in the chromosome (thus restoring the strain to the wild-type phenotype) and enabling the identification of strains with the Δcya mutation after transductions Luria broth cultures of χ3803 and χ4325 were transduced with P22HTint propagated on S. typhimurium χ3670, which contains the plasmid pSD110. Selection was made on MacConkey agar+1% maltose+100 μg ampicillin/ml. After 26 h, an ampicillin-resistant, Mal$^+$ colony of each strain was picked and purified on Macconkey agar+1% maltose agar and designated χ3824 (ty2) and χ4331 (ISP1820) which have the genotype Δcrp-10 Δ[zhc-1431::Tn10] pSD110$^+$.

Strains χ3824 and χ4331 were grown in L broth+100 μg ampicillin/ml and were each independently transduced with P22HTint propagated on χ3712 to introduce the Δcya-12 and the linked zid-62::Tn10 mutations. Selection for a maltose negative, tetracycline resistance, ampicillin resistance phenotype was made on MacConkey agar+1% maltose+100 μg ampicillin/ml+12.5 μg tetracycline/ml. Ampicillin-resistant (pDS110$^+$), tetracycline-resistant (zid-62::Tn10), Mal$^-$ (Δcya) colonies were picked and purified onto MacConkey agar+1% maltose+100 μg ampicillin/ml+12.5 μg tetracycline/ml. Purified colonies were picked into Luria broth, grown to turbidity and the strains checked for complete LPS, Vi antigen and auxotrophy for arginine, cysteine and tryptophan. Isolates of the correct phenotype were designated χ3919 (Ty2) and χ4340 (ISP1820) which have the genotype Δcrp-10 Δ[zhc-1431::Tn10] pSD110$^+$ Δcya-12 zid-62::Tn10. Cultures of χ3919 and χ4340 were grown in L broth+100 μg ampicillin/ml+12.5 μg tetracycline/ml to turbidity, diluted 1:10 into BSG, and 100 μl samples of each culture spread onto fusaric-containing media and incubated approximately 36 h at 37° C. Fusaric acid-resistant colonies of each strain were picked and purified onto FA media. Purified FA-resistant colonies were picked into Luria broth, grown to turbidity and then checked for loss of Tn10 (tetracycline sensitivity), complete LPS, Vi antigen and auxotrophy for arginine, cysteine and tryptophan. The pSD110 plasmid was spontaneously lost during growth of the strains in the absence of ampicillin. The final strains which were ampicillin-sensitive and plasmid-free were designated χ3924 (ty2) and χ4345 (ISP1820) which have the genotype Δcrp-10 Δ[zhc-1431::Tn10] Δcya-12 Δ[zid-62::Tn10]. Since synthesis of flagella with display of motility is partially dependent upon functional cya and crp genes and since flagella are important antigens, we selected derivatives of χ3924 and χ4346 that possess a suppressor mutation (cfs) that permits flagella synthesis and function to be independent of the cya and crp gene functions. χ4073 was selected as a flagella-positive derivative of χ3924, and χ4346 was selected as a flagella-positive derivative of χ4345. Table 10 lists. the wild-type parent strains and their Δcya Δcrp derivatives.

Strains χ4073 and χ4346 can easily be distinguished from their wild-type parents by the following phenotypic characteristics: the inability to ferment or grow on the carbon sources maltose, mannitol, sorbitol, melibiose and xylose, inability to produce $H_2S$, increased generation time, and the significantly increased murine $LD_{50}$ values.

TABLE 10

Bacterial Strains

χ3769, S. typhi Ty2

Type E1, wild type, Vi$^+$.
Received from L. Baron, Walter Reed Army Institute of Research, Washington, DC, as Ty2.
χ4073 S. typhi Ty2

Δcrp-10 [zhc-1431::Tn10] Δcya-12 Δ[zid-62::Tn10]; Crp$^-$ Cdt$^-$ Cya$^-$Arg$^-$ derivative of χ3769.
χ3744 S. typhi ISP1820

Type 46, wild type, Vi$^+$.
Received from M. Levine, Center for Vaccine Development, Baltimore, MD, as ISP1820. 1983 isolate from a Chilean patient.
χ4346 S. typhi ISP1820

Δcrp-10 Δ[zhc-1431::Tn10] Δcya-12 Δ[zid-62::Tn10]; Crp$^-$ Cdt$^-$ Cya$^-$ Arg$^-$ derivative of χ3744.

Growth conditions for χ3744, χ3769, χ4073 and χ4346

Cells of each strain were picked from agar medium into 2 ml Luria broth. Cultures were incubated as static cultures at 37° C. for approximately 14 h. When the cultures were visibly turbid ($OD_{600} \geq 0.5$), a loopful of each culture was streaked for isolated colonies on the media listed in Table 11 to verify some of the phenotypic properties. Cultures were also tested for sensitivity to phages, antibiotic susceptibility, ability to produce wild-type LPS, auxotrophy, motility, inability to produce colicins, absence of plasmid DNA, mean generation time, and agglutination by antisera to identify the O, H and Vi antigen of S. typhi (see Table 11). The phenotypic properties of all strains were as expected with the Δcya Δcrp strains χ4346 and χ4073 growing significantly more slowly than their wild-type parents.

TABLE 11

Phenotypic characterization of S. typhi wild-type and Δcrp-10 Δcya-12 strains

| | Phenotype | | | |
|---|---|---|---|---|
| | χ3744 | χ4346 | χ3769 | χ4073 |
| MacConkey Base Agar + | | | | |
| 1% maltose | + | − | + | − |
| 1% sorbitol | + | − | + | − |
| 1% mannitol | + | − | + | − |
| 1% melibiose | + | − | + | − |
| 1% rhamnose | − | − | − | − |
| 1% citrate | − | − | − | − |
| 1% arabinose | − | − | − | − |
| 1% mannose | + | + | + | + |
| 1% xylose | + | − | + | − |
| 1% glucose | + | + | + | + |
| Minimal agar[a] + | | | | |
| 0.5% glucose | + | + | + | + |
| 0.5% sorbitol | + | − | + | − |
| 0.5% mannitol | + | − | + | − |
| 0.5% melibiose | + | − | + | − |
| 0.5% rhamnose | − | − | − | − |
| 0.5% citrate | − | − | − | − |
| 0.5% arabinose | − | − | − | − |
| 0.5% mannose | + | + | + | + |
| 0.5% xylose | + | − | + | − |

TABLE 11-continued

Phenotypic characterization of S. typhi wild-type and Δcrp-10 Δcya-12 strains

| | Phenotype | | | |
|---|---|---|---|---|
| | χ3744 | χ4346 | χ3769 | χ4073 |
| Triple sugar Iron media - H$_2$S production | + | − | + | − |
| alkaline slant = | Lac$^-$ Glu$^+$ Suc$^-$ | Lac$^-$ Glu$^+$ Suc$^-$ | Lac$^-$ Glu$^+$ Suc$^-$ | Lac$^-$ Glu$^+$ Suc$^-$ |
| Indole fermentation assay | − | − | − | − |
| Bacteriophage sensitivity[c] | | | | |
| ViII | S | S | S | S |
| Felix-O | S | S | S | S |
| P22HTint | S | S | S | S |
| P1L4 | R | R | R | R |
| L | R | R | R | R |
| KB1 | R | R | R | R |
| LPS profile by SDS-PAGE (silver stain) (comp. = complete) | comp. | comp. | comp. | comp. |
| Motility[d] | + | + | + | + |
| Colicin(s) production | − | − | − | − |
| MGT[e] | 26.6 | 36.5 | 24.3 | 34.5 |
| Plasmid content | none | none | none | none |
| Auxotrophy | Cys$^-$ Trp$^-$ Arg$^+$ | Cys$^-$ Trp$^-$ Arg$^+$ | Cys$^-$ Trp$^-$ Arg$^+$ | Cys$^-$ Trp$^-$ Arg$^+$ |
| MIC[f] | | | | |
| Tetracycline | 4 | 4 | <2 | 4 |
| Streptomycin | 64 | 64 | 16 | 8 |
| Ampicillin | <2 | <2 | <2 | <2 |
| Gentamicin | <2 | <2 | <2 | <2 |
| Chloramphenicol | 4 | 4 | 4 | 4 |
| Neomycin | <2 | <2 | <2 | <2 |
| Rifampicin | 8 | 16 | 8 | 8 |
| Nalidixic acid | <2 | 4 | <2 | 4 |
| Spectinomycin | 32 | 32 | 32 | 16 |
| Kanamycin | <2 | <2 | <2 | <2 |
| Agglutination with Difco antisera to: | | | | |
| flagellar antigen H:1 | + | + | + | + |
| flagellar antigen H:2 | + | + | + | + |
| Group D factor 9 | + | + | + | + |
| Group D factor 12 | + | + | + | + |
| Group D (0−1,9,12) | + | + | + | + |

[a]Minimal media recipe attached; supplements include L-arginine HCl 22 μg/ml, L-cysteines HCl 22 μg/ml, L-tryptophan 20 μg/ml.
[c]phage sensitivity was assayed by soft agar overlay technique of by transduction. S = sensitive; R = resistant.
[d]Motility determined by stabbing a loopful of a standing-overnight Luria broth culture into media containing 1.0% casein, 0.5% NaCl, 0.5% Difco agar and 50 μg/mg triphenyl-tetrazoleum chloride; incubation at 37° C. and motility recorded at 24 and 48 h.
[e]Mean Generation Time (min.) = determined in Luria broth with aeration (150 rpm New Brunswick platform shaker) at 37° C.
[f]Minimal Inhibitory Concentrations (μg/ml) of antibiotics were determined by streaking standing-overnight cultures of each strain onto agar containing defined concentrations of antibiotics.

Growth characteristics on agar media

Strains were grown in Luria broth as standing-overnight cultures at 37° C., diluted in buffered saline and gelatin (BSG) and plated on MacConkey agar containing 1% maltose to achieve isolated colony-forming units (cfu). All colonies of a given strain appear uniform in size and color. Due to the slower growth rates of Δcya crp strains compared to their wild-type parents, growth on MacConkey media takes ~36+ h at 37° C. before colonies of χ4073 and χ4346 are easily visible.

Stability of mutant phenotypes

Fifty-fold concentrated cultures and various dilutions (~10$^9$, 10$^7$, 10$^5$, 10$^3$ cfu/plate) of χ4073 and χ4346 were plated on minimal agar media (supplemented with 22 μg L-arginine/ml, 22 μg L-cysteine/ml and 20 μg L-tryptophan/ml) containing either 0.5% maltose, melibiose, xylose, glycerol, or rhamnose that should not support their growth. One set of duplicate plates were UV-irradiated (5 joules/meter $^2$/sec) and incubated at 37° C. in the dark. The other set was incubated at 37° C. with illumination. No revertants and/or mutants were detected after a 48 h growth period.

Storage of strains

Each strain was maintained in a 1% peptone-5% glycerol suspension and stored at −70° C.

Preparation of inoculum for animal experimentation

The following is a standardized protocol for growth and suspension of each vaccine strain and its parent for intraperitoneal (i.p.) inoculation of mice.

Female CFW mice (18–20 g) (Charles River, Wilmington, Mass.) were used for determining LD$_{50}$ values of wild-type S. typhi and virulence of the Δcrp-10 Δcya-12 derivatives. Static overnight cultures (37° C.) were diluted 1:20 into prewarmed Luria broth and aerated (150 rpm) at 37° C. until an OD$_{600}$ of ≦0.08 was reached. Wild-type and Δcrp-10 Δcya-12 S. typhi cells were suspended in 15% (wt/vol) hog gastric mucin (American Laboratories, Omaha, Nebr.). The 15% mucin suspension was prepared by neutralizing to pH 7, autoclaving 10 min at 121° F. at 15 p.s.i., and 3 μg of freshly prepared sterile ferric ammonium citrate/ml (Sigma, St. Louis, Mo.) was added prior to adding appropriately diluted S. typhi cells. The cell suspensions were then administered i.p. to CFW mice through a 23-gauge needle in 500 μl volumes. LD$_{50}$ values of the wild-type parents and the Δcrp-10 Δcya-12 derivatives were determined after recording mortality data for 72 h. See Table 12 for results on virulence of S. typhi mutants relative to wild-type parents.

TABLE 12

Virulence of ISP1820 and Ty2 S. typhi wild-type and Δcrp-11 Δcrp-10 strains

| Strain No. | Genotype | LD$_{50}$[1] CFU |
|---|---|---|
| χ3744 | ISP1820 wild type | 32 |
| χ4299 | Δcrp-11 Δ[zhc-1431::Tn10] | <600 |
| χ4300 | Δcrp-11 Δ[zhc-1431::Tn10]/ pSD110$^{+2}$ | 107 |
| χ4323 | Δcrp-11 Δ[zhc-1431::Tn10] Δcya-12 Δ[zid-62::Tn10] | >2.8 × 10$^3$ |
| χ4325 | Δcrp-10 Δ[zhc-1431::Tn10] | >3.2 × 10$^6$ |
| χ4331 | Δcrp-10 Δ[zhc-1431::Tn10]/ pSD110$^+$ | >2.3 × 10$^5$ |
| χ4346 | Δcrp-10 Δ[zhc-1431::Tn10] Δcya-12 Δ[zid-62::Tn10] | 4.4 × 10$^5$ |
| χ3769 | Ty2 wild type | 54 |
| χ3878 | Δcrp-11 Δ[zhc-1431::Tn10] | 1.0 × 10$^3$ |
| χ3880 | Δcrp-11 Δ[zhc-1431::Tn10]/ pSD110$^+$ | <19 |
| χ3927 | Δcrp-11 Δ[zhc-1431::Tn10] Δcya-12 Δ[zid-62::Tn10] | 1.1 × 10$^4$ |
| χ3803 | Δcrp-10 Δ[zhc-1431::Tn10] | 1.5 × 10$^5$ |
| χ3824 | Δcrp-10 Δ[zhc-1431::Tn10]/ pSD110$^+$ | >1.9 × 10$^5$ |
| χ4073 | Δcrp-10 Δ[zhc-1431::Tn10] Δcya-12 Δ[zid-62::Tn10] | >1.0 × 10$^5$ |

[1]LD$_{50}$ calculated by method of Reed and Muench (1938. Am. J. Hyg. 27:493–497.) Morbidity and mortality data collected over a 72 h period.
[2]pSD110 (Schroeder, C. J., and W. J. Dobrogosz. 1986. J. Bacteriol. 167;616–622) is a pBR322 derivative containing the wild-type crp$^+$ gene and its promoter from S. typhimurium. Previous virulence assays have shown this plasmid to complement a crp mutation in S. choleraesuis, S. typhimurium and S. typhi and restore virulence to wild-type levels.

Mammalian cell culture adherence and invasion assays

Data on the ability of Δcrp-10 Δcya-12 and Δcrp-11 Δcya-12 strains to adhere to and invade CHO cells as compared to the wild-type parent strains are presented in Table 13. The *S. typhi* mutants show a reduced capability to adhere to and/or invade monolayers of CHO cells over a 2-h and 4-h period, respectively, at 37° C. as compared to the wild-type parent strains.

TABLE 13

Adherence and invasion of CHO cell monolayers by *S. typhi* wild-type and Δcrp Δcya strains

| Strain No. | Genotype | Percent adherence[1] | Percent invasion[2] |
|---|---|---|---|
| χ3744 | wild type | 43.5~6.5 | 34.2~8.3 |
| χ4323 | Δcrp-11 Δ[zhc-1431::Tn10] Δcya-12 Δ[zid-62::Tn10] | 20.8~1.6 | 8.3~0.4 |
| χ4346 | Δcrp-10 Δ[zhc-1431::Tn10] Δcya-12 Δ[zid-62::Tn10] | 8.3~0.7 | 5.3~2.2 |

[1]Percentage of inoculum adhered to cells after incubation for 2 h.
[2]Percentage of inoculum recovered from CHO cells 2 h after incubation in 100 μg gentamicin/ml. Values are mean ~ SD of triplicate samples.

Growth and persistence of mutants in normal human sera as compared to wild-type parents Growth curves were performed in normal human sera that has previously been adsorbed with wild-type *S. typhi*. Approximately $10^6$ cfu of *S. typhi* Δcya Δcrp and wild-type strains were added to each ml of sera that had been equilibrated with HEPES at 37° C. in a 5% $CO_2$ chamber. Complement-mediated bacteriolysis activity was verified by inactivating sera at 60° C. for 10 min and checking growth of *E. coli* K-12 after 60 min. In normal sera, *E. coli* K-12 cells were killed in sera after 60 min.

More specifically, χ3744 (ISP1820, wild type), χ3769 (Ty2, wild type), χ4073 (Ty2 Δcya-12 Δ[crp-cysG]-10), χ4346 (ISP1829 Δcya-12 Δ[crp-cysG]-10), and χ289 (*E. coli* K-12) were grown in Luria broth as standing overnight cultures at 37° C. Human serum was adsorbed with the homologous wild-type *S. typhi* Ty2 and ISP 1820 strains χ3769 and χ3744, respectively, buffered with 20 mM HEPES and incubated in a 5 $CO_2$ atmosphere for assays. The *E. coli* K-12 χ289 strain represented a positive control for complement mediated bacteriolysis and the same strain when grown in heat-inactivated serum served as the negative control as is evident by net growth.

FIG. 5 shows the net growth and/or persistence of each strain over a 24-h period at 37° C.

Deposits of Strains. The following listed materials are on deposit under the terms of the Budapest Treaty, with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit, or for the enforceable life of the U.S. patent, whichever is longer. Should a culture become nonviable or be inadvertently destroyed, or, in the case of plasmid-containing strains, lose its plasmid, it will be replaced with a viable culture(s) of the same taxonomic description. The deposited materials mentioned herein are intended for convenience only, and are not required to practice the present invention in view of the description herein, and in addition, these materials are incorporated herein by reference.

| Strain | Deposit Date | ATCC No. |
|---|---|---|
| χ3958 | November 2, 1990 | 55224 |
| χ4323 | November 2, 1990 | 55115 |
| χ3926 | November 2, 1990 | 55112 |
| χ3927 | November 2, 1990 | 55117 |
| χ4297 | November 2, 1990 | 55111 |
| χ4346 | November 2, 1990 | 55113 |
| χ3940 | November 2, 1990 | 55119 |
| χ4073 | November 2, 1990 | 55118 |
| ISP2822 | November 2, 1990 | 55114 |
| ISP1820 | November 2, 1990 | 55116 |
| χ4417 | | |
| χ4435 | | |

Commercial Utility

The strains provided herein are directly and indirectly suitable for the production of immunogenic compositions, including vaccines, to prevent diseases caused by *S. typhi*, and other enteric bacteria with which antibodies to *S. typhi* cross react. These strains are also useful as carrier microorganisms for the production of expression products encoded on recombinant genes in the bacterial cells. In addition, the strains which can be used with enhanced safety are useful for the production of antibodies, both monoclonal and polyclonal, against *S. typhi*, and against antigens which are expressed in the avirulent *S. typhi.*

We claim:

1. An immunogenic composition for the immunization of an individual comprising a derivative of a pathogenic gram negative bacteria made avirulent by an inactivating mutation in a cya gene, in a pharmaceutically acceptable carrier.

2. An immunogenic composition for the immunization of an individual according to claim 1, wherein the avirulent derivative of a pathogenic gram negative bacteria is capable of expressing a recombinant gene derived from an agent which is pathogenic to said individual, to produce an antigen capable of inducing an immune response in said vertebrate against said pathogenic agent.

3. A method for stimulating the immune system to respond to an immunogenic antigen of a pathogenic gram negative bacteria comprising administering to said individual the immunogenic composition of claim 1.

4. A method for stimulating the immune system to respond to an immunogenic antigen of a pathogen comprising administering to said individual the immuniogenic composition of claim 2.

5. An isolated gram negative bacterial strain comprising a derivative of a pathogenic gram negative bacteria made avirulent by an inactivating mutation in a cya gene wherein said derivative is capable of invading and persisting in the gut-associated lymphoid tissue or bronchus-associated lymphoid tissue.

6. The isolated bacterial strain of claim 5 which is capable of expressing a recombinant gene derived from an agent which is pathogenic to an individual, to produce an antigen capable of inducing an immune response in said individual against said pathogenic agent.

7. A strain according to claim 6, wherein the avirulent strain of the pathogenic microbe contains a chromosomal mutation which is lethal, balanced by a vector which complements the lethal mutation to constitute a balanced lethal host-vector system.

8. A strain according to claim 7, wherein cells of the strain:

a) lack a functioning native chromosomal gene encoding beta-aspartate semialdehyde dehydrogenase (Asd);
b) have present a recombinant gene encoding a functional Asd polypeptide which complements the chromosomal asd mutation, but which cannot replace the defective chromosomal gene by recombination;
c) have a physical linkage between the recombinant genes encoding the functional Asd polypeptide and the immunogenic antigen, wherein the loss of the recombinant gene encoding the functional Asd polypeptide causes the cells to lyse when the cells are in an environment in which the lack of functional Asd causes the cells to lyse.

9. A method of utilizing a strain of a pathogenic gram negative bacteria made avirulent by a mutation in a cya gene, the method comprising preparing an immunogenic composition by combining the strain with a pharmaceutically acceptable carrier.

* * * * *

UNITED STATES PATENT AND TRADEMARK OFFICE
CERTIFICATE OF CORRECTION

PATENT NO.    : 5,855,880
DATED         : January 5, 1999
INVENTOR(S)   : Curtiss III et al.

It is certified that error appears in the above-identified patent and that said Letters Patent is hereby corrected as shown below:

Title page,
Item [19], United States Patent, the name of the Patentee should appear as
-- Curtiss III --.
Item [75], Inventors, should read -- Roy Curtiss III of St. Louis, MO --; and "Sandra M. Kelly" should be deleted.

Signed and Sealed this

Sixth Day of April, 2004

JON W. DUDAS
*Acting Director of the United States Patent and Trademark Office*